US012788620B2

(12) United States Patent
Huggins et al.

(10) Patent No.: US 12,788,620 B2
(45) Date of Patent: Nov. 10, 2026

(54) PERSONAL COOLING AND HEATING APPARATUS AND SYSTEM

(71) Applicant: AC Chair LLC, Mableton, GA (US)

(72) Inventors: Mark Huggins, Hilton Head Island, SC (US); Aaron Carmack, Mableton, GA (US); Jason Porter Whitmire, Greenville, SC (US)

(73) Assignee: AC Chair LLC, Mableton, GA (US)

( * ) Notice: Subject to any disclaimer, the term of this patent is extended or adjusted under 35 U.S.C. 154(b) by 930 days.

(21) Appl. No.: 17/898,004

(22) Filed: Aug. 29, 2022

(65) Prior Publication Data

US 2023/0065151 A1 Mar. 2, 2023

Related U.S. Application Data

(60) Provisional application No. 63/335,592, filed on Apr. 27, 2022, provisional application No. 63/303,851,
(Continued)

(51) Int. Cl.
*A61F 7/00* (2006.01)

(52) U.S. Cl.
CPC ............ *A61F 7/0053* (2013.01); *A61F 7/007* (2013.01); *A61F 7/0085* (2013.01);
(Continued)

(58) Field of Classification Search
CPC .... A61F 7/50053; A61F 7/007; A61F 7/0085; A61F 2007/0024; A61F 2007/0039; A61F 2007/0056; A61F 2007/0093
See application file for complete search history.

(56) References Cited

U.S. PATENT DOCUMENTS 3,738,367 A * 6/1973 Hardy ........................ A61F 7/02
607/104
4,141,585 A 2/1979 Blackman
(Continued)

FOREIGN PATENT DOCUMENTS

WO 2014105039 A1 7/2014

OTHER PUBLICATIONS

International search report, International application No. PCT/US22/41917. Date of mailing: Dec. 28, 2022. ISA/US, Alexandria, VA.
(Continued)

*Primary Examiner* — Joanne M Rodden
*Assistant Examiner* — Alyssa M Pape
(74) *Attorney, Agent, or Firm* — Gregory Finch; Finch Paolino, LLC

(57) ABSTRACT

A personal heating and cooling system comprising a chair, a pad comprising a length of flexible tubing and at least one heating element housed in an interior area of the pad, a pump configured to pump a volume of coolant (e.g., water) through the length of the flexible tubing, an intake trunk coupled to the pump and configured to deliver a volume of water from a reservoir (e.g., from a thermal insulated cooler) and a battery pack operably engaged with the pump and the at least one heating element. In certain embodiments, the pad may be integral to the chair and comprise seat and back portions of the chair. In certain embodiments, the pad may be removably coupled to the chair or other seating surface or may be laid flat.

16 Claims, 37 Drawing Sheets

Related U.S. Application Data filed on Jan. 27, 2022, provisional application No. 63/292,321, filed on Dec. 21, 2021, provisional application No. 63/238,094, filed on Aug. 27, 2021.

(52) U.S. Cl.
CPC ................. *A61F 2007/0024* (2013.01); *A61F 2007/0039* (2013.01); *A61F 2007/0056* (2013.01); *A61F 2007/0093* (2013.01)

(56) References Cited

U.S. PATENT DOCUMENTS

| | | | | |
|---|---|---|---|---|
| 4,691,762 | A | 9/1987 | Elkins et al. | |
| 5,865,841 | A * | 2/1999 | Kolen | A61H 9/0078 607/104 |
| 6,302,094 | B1 | 10/2001 | Wehrly et al. | |
| 7,866,743 | B1 | 1/2011 | Russell et al. | |
| 2004/0068310 | A1* | 4/2004 | Edelman | A61F 7/02 607/104 |
| 2006/0048520 | A1 | 3/2006 | Huang et al. | |
| 2007/0068651 | A1* | 3/2007 | Gammons | A61F 7/02 607/108 |
| 2007/0257018 | A1* | 11/2007 | Huang | H05B 1/0272 219/217 |
| 2008/0060374 | A1* | 3/2008 | Gammons | F25D 3/08 607/104 |
| 2008/0314370 | A1 | 12/2008 | Weiche | |
| 2015/0289666 | A1 | 10/2015 | Chandler et al. | |
| 2015/0290065 | A1* | 10/2015 | Augustine | A61G 7/05 5/655.3 |
| 2019/0045936 | A1* | 2/2019 | Muller | F25D 31/002 |
| 2020/0121544 | A1* | 4/2020 | George | G16H 20/70 |
| 2020/0375793 | A1* | 12/2020 | Dilligan | A61F 7/10 |
| 2020/0376922 | A1 | 12/2020 | Bhandari et al. | |
| 2023/0226308 | A1* | 7/2023 | Traweek | A61B 5/6891 600/27 |

OTHER PUBLICATIONS

Written Opinion of the International Searching Authority, International application No. PCT/US22/41917. Date of mailing: Dec. 28, 2022. ISA/US, Alexandria, VA.

Extended European Search Report, European application No. 22862176.9. Date of mailing: Dec. 9, 2025. European Patent Office, Munich, DE.

* cited by examiner

1500

1600

1700

1800

1900

PERSONAL COOLING AND HEATING APPARATUS AND SYSTEM

CROSS-REFERENCE TO RELATED APPLICATIONS

This application claims priority benefit of U.S. Provisional Application Ser. No. 63/238,094, filed Aug. 27, 2021, entitled "BATTERY-OPERATED PORTABLE COOLING SYSTEM AND APPARATUS"; and also claims priority benefit of U.S. Provisional Application Ser. No. 63/292,321, filed Dec. 21, 2021, entitled "BATTERY-OPERATED PORTABLE COOLING SYSTEM AND APPARATUS"; and also claims priority benefit of U.S. Provisional Application Ser. No. 63/303,851, filed Jan. 27, 2022, entitled "BATTERY-OPERATED PORTABLE COOLING SYSTEM AND APPARATUS"; and also claims priority benefit of U.S. Provisional Application Ser. No. 63/335,592, filed Apr. 27, 2022, entitled "Dual Heating and Cooling Chair and Pad"; the entireties of which are hereby incorporated herein at least by virtue of this reference.

FIELD

The present disclosure relates to the field of personal heating and cooling systems; in particular, a personal heating and cooling apparatus and system configured to interface with a thermal insulated cooler.

BACKGROUND

People engaging in various outdoor activities such as hunting, fishing, tailgating or attending sporting events often sit outdoors in portable chairs for prolonged durations. Sitting outdoors during colder months can be extremely uncomfortable, and additional layers of clothing or blankets are often insufficient, uncomfortable and/or and cumbersome to transport. When a person is seated outdoors during warmer months, little can be done to minimize discomfort and overheating. Accordingly, there is currently a need for improved personal heating and cooling systems that can be adjusted according to ambient conditions.

Through applied effort, ingenuity, and innovation, Applicant has identified a number of deficiencies and problems with personal heating and cooling systems. Applicant has developed a solution that is embodied by the present invention, which is described in detail below.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Certain aspects of the present disclosure provide for a personal heating and cooling system, comprising an elongated pad comprising an upper fabric surface, a lower fabric surface and a connector portion configured to be selectively coupled to a surface of a chair, wherein the elongated pad is configured to be disposed on a back portion and a seat portion of the chair when the connector portion is selectively coupled to the surface of the chair, wherein the elongated pad comprises a length of flexible tubing disposed on an internal area of the elongated pad and housed between the upper fabric surface and the lower fabric surface, wherein the length of flexible tubing extends between a first end comprising a water inlet and a second end comprising a water outlet, wherein the elongated pad comprises at least one heating pad coupled to the internal surface of the elongated pad between the upper fabric surface and the lower fabric surface; an intake trunk comprising a water supply line and a water return line; a pump comprising a first coupling configured to be selectively coupled with the first end and the second end of the length of flexible tubing and a second coupling configured to be removably coupled with the water supply line and the water return line of the intake trunk, wherein the pump is operably configured to circulate a volume of water from the water supply line of the intake trunk through the length of flexible tubing and to the water return line of the intake trunk; and a battery pack operably engaged with the pump and the heating pad to provide a flow of power to the pump and the heating pad.

In accordance with certain embodiments of the personal heating and cooling system, the intake trunk may comprise an adapter portion coupled to a first end of the intake trunk. The adapter portion may comprise a filter assembly configured to facilitate a flow of water from an insulated cooler to the intake trunk. The adapter portion may be configured to selectively interface with a drain portion of the insulated cooler to facilitate the flow of water from the insulated cooler to the intake trunk. In certain embodiments, the personal heating and cooling system may further comprise a bridge portion selectively coupled to the intake trunk. The bridge portion may be configured to be selectively coupled to a wall of an insulated cooler. In certain embodiments, the personal heating and cooling system may further comprise at least one controller operably engaged with the battery pack. The at least one controller may be configured to regulate the flow of power to the pump and the heating pad in response to at least one user input. In certain embodiments, the personal heating and cooling system may further comprise at least one thermal sensor communicably engaged with the at least one controller. The at least one controller may be configured to regulate the flow of power to the pump and the heating pad in response to an input from the at least one thermal sensor. In certain embodiments, the at least one heating pad may comprise a first heating zone and a second heating zone, wherein the at least one controller is configured to selectively regulate the flow of power between the first heating zone and the second heating zone.

Further aspects of the present disclosure provide for a personal heating and cooling system, comprising a chair comprising a foldable frame and a fabric surface coupled to the foldable frame to comprise a chair back and a chair seat, wherein the fabric surface comprises an upper fabric layer and a lower fabric layer, wherein the foldable frame is configurable between a folded position and an open position, wherein the chair comprises a length of flexible tubing disposed on an internal area of the chair between the upper fabric layer and the lower fabric layer, wherein the length of flexible tubing extends between a first end comprising a water inlet and a second end comprising a water outlet, wherein the flexible tubing is vertically oriented such that the flexible tubing does not kink when the foldable frame is configured in the folded position, wherein the chair comprises at least one heating pad disposed on the internal area of the chair between the upper fabric layer and the lower fabric layer; a pump comprising a coolant outlet coupled to the first end of the flexible tubing and coolant inlet coupled to a water supply line, wherein the pump is configured to pump a volume of water from the water supply line through the length of flexible tubing between the first end and the second end of the flexible tubing; and a battery pack operably engaged with the pump and the heating pad to provide a flow of power to the pump and the heating pad.

In accordance with certain embodiments of the personal heating and cooling system, the pump may be selectively coupled to a portion of the fabric surface of the chair. In certain embodiments, the chair may further comprise a cooler portion coupled to the chair back, wherein the water supply line and the water outlet extend to an interior portion of the cooler. In certain embodiments, the personal heating and cooling system may further comprise at least one controller operably engaged with the battery pack. The at least one controller may be configured to regulate the flow of power to the pump and the heating pad in response to at least one user input. In certain embodiments, the personal heating and cooling system may further comprise at least one pressure sensor communicably engaged with the at least one controller. The at least one controller may be configured to regulate the flow of power to the pump and the heating pad in response to an input from the at least one pressure sensor. In certain embodiments, the personal heating and cooling system may further comprise at least one thermal sensor communicably engaged with the at least one controller. The at least one controller may be configured to regulate the flow of power to the pump and the heating pad in response to an input from the at least one thermal sensor. In certain embodiments, the at least one heating pad may comprise a first heating zone and a second heating zone. The at least one controller may be configured to selectively regulate the flow of power between the first heating zone and the second heating zone.

Still further aspects of the present disclosure may provide for a personal heating and cooling system, comprising a chair comprising a foldable frame and a fabric surface coupled to the foldable frame to comprise a chair back and a chair seat, wherein the fabric surface comprises an upper fabric layer and a lower fabric layer, wherein the foldable frame is configurable between a folded position and an open position, wherein the chair comprises a length of flexible tubing disposed on an internal area of the chair between the upper fabric layer and the lower fabric layer, wherein the length of flexible tubing extends between a first end comprising a water inlet and a second end comprising a water outlet, wherein the flexible tubing is vertically oriented such that the flexible tubing does not kink when the foldable frame is configured in the folded position, wherein the chair comprises at least one heating pad disposed on the internal area of the chair between the upper fabric layer and the lower fabric layer; a pump housing comprising a bottom, side walls, and a top defining an interior chamber and an exterior surface, wherein the exterior surface comprises a heat exchanger; a pump housed in the interior chamber of the pump housing, the pump comprising a coolant outlet coupled to the first end of the flexible tubing and a coolant inlet coupled to the second end of the flexible tubing, wherein the pump is operably configured to circulate a volume of water through the flexible tubing, wherein the pump and the flexible tubing are configured as a closed loop; and a battery pack operably engaged with the pump and the heating pad to provide a flow of power to the pump and the heating pad.

In accordance with certain embodiments, the personal heating and cooling system may further comprise a heat exchanger coil disposed in the interior chamber of the pump housing. In said embodiments, the coolant inlet may comprise a first end of the heat exchanger coil and the coolant outlet may comprise a second end of the heat exchanger coil. In certain embodiments, the personal heating and cooling system may further comprise at least one controller operably engaged with the battery pack. The at least one controller may be configured to regulate a flow of power to the pump and the heating pad in response to at least one user input. In certain embodiments, the personal heating and cooling system may further comprise at least one pressure sensor communicably engaged with the at least one controller. In said embodiments, the at least one controller may be configured to regulate the flow of power to the pump and the heating pad in response to an input from the at least one pressure sensor. In certain embodiments, the personal heating and cooling system may further comprise at least one thermal sensor communicably engaged with the at least one controller. In said embodiments, the at least one controller may be configured to regulate the flow of power to the pump and the heating pad in response to an input from the at least one thermal sensor. In certain embodiments, the at least one heating pad may comprise a first heating zone and a second heating zone. The at least one controller may be configured to selectively regulate the flow of power between the first heating zone and the second heating zone.

The foregoing has outlined rather broadly the more pertinent and important features of the present invention so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent structures do not depart from the spirit and scope of the invention as set forth in the appended claims.

BRIEF DESCRIPTION OF DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

Figure 1A:
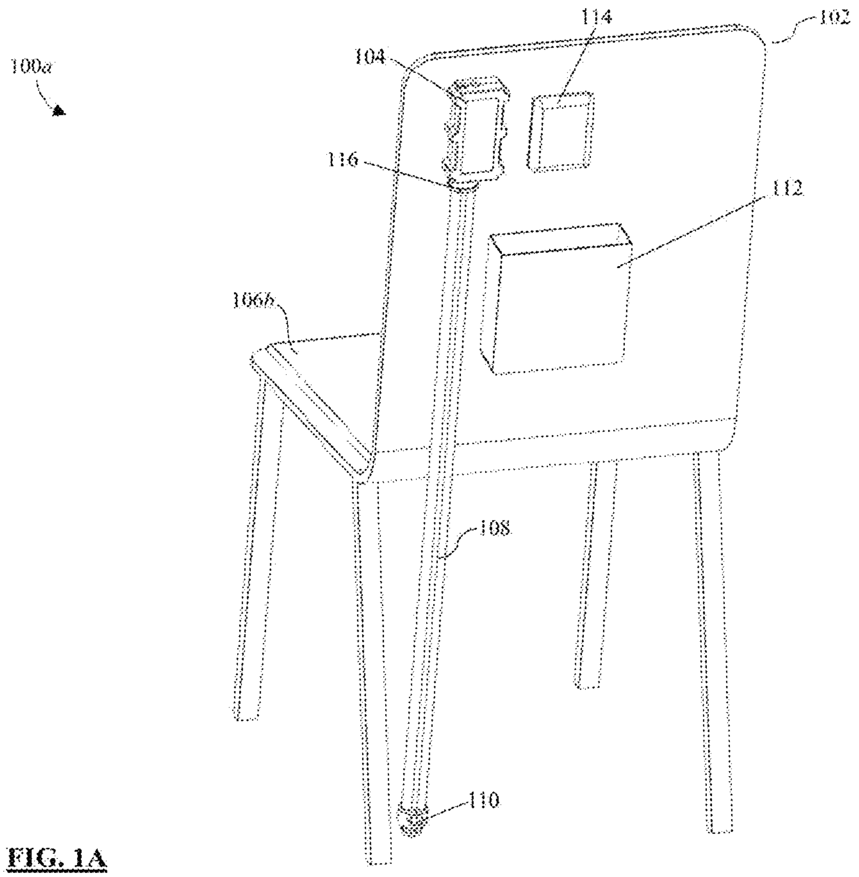
FIG. 1A is a perspective view of a personal heating and cooling apparatus, in accordance with certain aspects of the present disclosure.

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Where possible, any terms expressed in the singular form herein are meant to also include the plural form and vice versa, unless explicitly stated otherwise. Also, as used herein, the term “a” and/or “an” shall mean “one or more,” even though the phrase “one or more” is also used herein. Furthermore, when it is said herein that something is “based on” something else, it may be based on one or more other things as well. In other words, unless expressly indicated otherwise, as used herein "based on" means "based at least in part on" or "based at least partially on." Like numbers refer to like elements throughout. All definitions, as defined and used herein, should be understood to control over dictionary definitions, definitions in documents incorporated by reference, and/or ordinary meanings of the defined terms.

Following below are more detailed descriptions of various concepts related to, and embodiments of, inventive methods, devices and systems configured to provide for a personal heating and cooling system comprising a chair, a pad comprising a length of flexible tubing and at least one heating element housed in an interior area of the pad, a pump configured to pump a volume of coolant (e.g., water) through the length of the flexible tubing, an intake trunk coupled to the pump and configured to deliver a volume of water from a reservoir (e.g., from a thermal insulated cooler) and a battery pack operably engaged with the pump and the at least one heating element.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The present disclosure should in no way be limited to the exemplary implementation and techniques illustrated in the drawings and described below.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein, "exemplary" means serving as an example or illustration and does not necessarily denote ideal or best.

As used herein, the term "includes" means includes but is not limited to, the term "including" means including but not limited to. The term "based on" means based at least in part on.

As used herein, the term "interface" refers to any shared boundary across which two or more separate components of a computer system may exchange information. The exchange can be between software, computer hardware, peripheral devices, humans, and combinations thereof. The term "interface" may be further defined as any shared boundary or connection between two dissimilar objects, devices or systems through which information or power is passed and/or a mechanical, functional and/or operational relationship is established and/or accomplished. Such shared boundary or connection may be physical, electrical, logical and/or combinations thereof.

As used herein, the term "connector" refers to any of various devices for connecting one object to another.

As used herein, the term "trunk" refers to any suitable structure for conveying a volume of liquid from a supply source or reservoir.

As used herein, the term "elongated" may mean any shape having a length, including, but not limited to, square, rectangular, oblong and the like.

Certain benefits and advantages of the present disclosure include a personal heating and cooling system comprising a reversible pad with a cooling function on a first side and a heating function on a second side. In certain embodiments, the cooling function may comprise a length of flexible tubing housed in an internal area of the pad. The length of flexible tubing may be routed in straight lines (i.e., perpendicular to each other) to minimize bending across tubes.

Certain benefits and advantages of the present disclosure include a personal heating and cooling system comprising a heated and cooled chair. In certain embodiments, the heated and cooled chair may comprise removeable cushions. In certain embodiments, the heated and cooled chair may comprise chair mounted controls for controlling one or more heating or cooling functions of the chair by at least one user. In certain embodiments, one or more coolant lines and/or one or more heating elements may extend through one or both arm rests of the heated and cooled chair.

Certain benefits and advantages of the present disclosure include a personal heating and cooling system comprising a pass-through drain plug adapter for selectively attaching a trunk to a drain plug of a thermal insulated cooler to enable coolant exchange between the thermal insulated cooler and a cooling chair comprising at least one integrated coolant line. In accordance with certain aspects of the present disclosure, the trunk may comprise a high R-value tubing combined with a neoprene jacket. The trunk may comprise intake and return lines that are separated within a jacket or other structure to prevent thermal crossover between the intake and return lines.

Certain benefits and advantages of the present disclosure include a personal heating and cooling system comprising a coupler and filter assembly configured to enable the trunk to be selectively coupled to a pump housing. In certain embodiments, the coupler may be configured to integrate dual water lines from the trunk. The filter assembly may comprise a removeable filter that may be selectively removed and re-installed by a user for cleaning or replacement.

Certain benefits and advantages of the present disclosure include a personal heating and cooling system comprising one or more power options for powering a pump and one or more heating elements. In certain embodiments, the power options may include a rechargeable battery bank and/or a wired wall adapter. The rechargeable battery bank may include at least one USB interface. In certain embodiments, the pump may comprise a voltage in the range of 3V to 12V.

Certain benefits and advantages of the present disclosure include a personal heating and cooling system comprising a heated and cooled pad comprising at least one connector portion for selectively coupling the heated and cooled pad to a chair or other surface. In certain embodiments, the at least one connector portion may comprise a hood structure configured to couple an upper portion of the heated and cooled pad to a back portion of the chair. In certain embodiments, the heated and cooled pad may comprise at least one non-slip material to aid in maintaining the pad in place when selectively coupled to the chair. In certain embodiments, the personal heating and cooling system may be configured to lay flat.

Certain benefits and advantages of the present disclosure include a personal heating and cooling system comprising a modular construction to enable ease of serviceability and replacement of components.

Certain benefits and advantages of the present disclosure include a personal heating and cooling system comprising an optimized ratio of thermal comfort zones; for example, more heating and cooling lines in the chair/pad back versus the chair/pad seat. In certain embodiments, the personal heating and cooling system may comprise at least one controller configured to selectively command the operation of the pump and the heating element(s) to optimize a heating or cooling cycle to gain the most comfort for the user over a given period of time. For example, balancing cooling/heating according to battery life; or balancing cooling according to ice retention from an attached thermal cooler. In certain embodiments, the personal heating and cooling system may comprise at least one thermal sensor configured to cycle the pump and/or the heating element(s) ON/OFF according to one or more thermostat presets and/or one or more safety or comfort threshold(s) (e.g., to prevent overheating). In certain embodiments, the personal heating and cooling system may comprise at least one occupant sensor (e.g., pressure sensor) to enable the controller to automatically engage/disengage the pump or the heating elements based on the presence of a user.

Certain benefits and advantages of the present disclosure include a personal heating and cooling system comprising a chair with an integrated cooler for retaining a volume of water and ice for cycling through one or more coolant lines of the chair via at least one pump. In accordance with certain embodiments, the at least one pump may comprise a diaphragm pump to enable quiet/efficient operation and the ability of the user to clear the one or more coolant lines. In certain embodiments, the one or more coolant lines may comprise a 1/16" internal diameter and 1/8" outer diameter tubing.

Certain benefits and advantages of the present disclosure include a personal heating and cooling system comprising a chair or pad with one or more integral coolant lines operably engaged with at least one pump. In certain embodiments, personal heating and cooling system may comprise a closed loop system wherein the one or more integral coolant lines are charged with a volume of coolant (e.g., water) that is cycled through the one or more integral coolant lines via the at least one pump. The at least one pump may be housed in a housing that may be submersible in a container holding a volume of cold water to enable heat transfer between the volume of coolant and the volume of cold water.

Certain benefits and advantages of the present disclosure include a personal heating and cooling system comprising one or more selectively attachable accessories, such as a drink holder comprising one or more heating or cooling elements and a blanket comprising one or more heating or cooling elements.

Turning now descriptively to the drawings, in which similar reference characters denote similar elements throughout the several views, FIGS. 1A-1H depict perspective views of a personal heating and cooling apparatus and system. In accordance with certain aspects of the present disclosure, the personal heating and cooling system described herein may comprise a chair (e.g., a foldable chair) or pad comprising a plurality of heating and cooling elements being integrally incorporate therein. In accordance with certain aspects of the present disclosure, the chair or pad may comprise at least one length of flexible tubing being housed in an internal area of the chair or pad and configured to pump a volume of coolant (e.g., water) via an interface with an electric pump. In accordance with certain aspects of the present disclosure, the electric pump may be configured to pump a volume of cold water from a reservoir (e.g., a thermal insulated cooler) through the at least one length of flexible tubing. One or more heating elements may be housed in the internal area of the chair or pad and may be operably engaged with a battery or power source to provide a heating output in response to at least one user input at a user interface. The user interface may be configured to command a controller operably engaged with the pump and the heating elements to selectively command one or more heating and cooling functions of the personal heating and cooling system in response to at least one user input at the user interface.

Figure 1B:
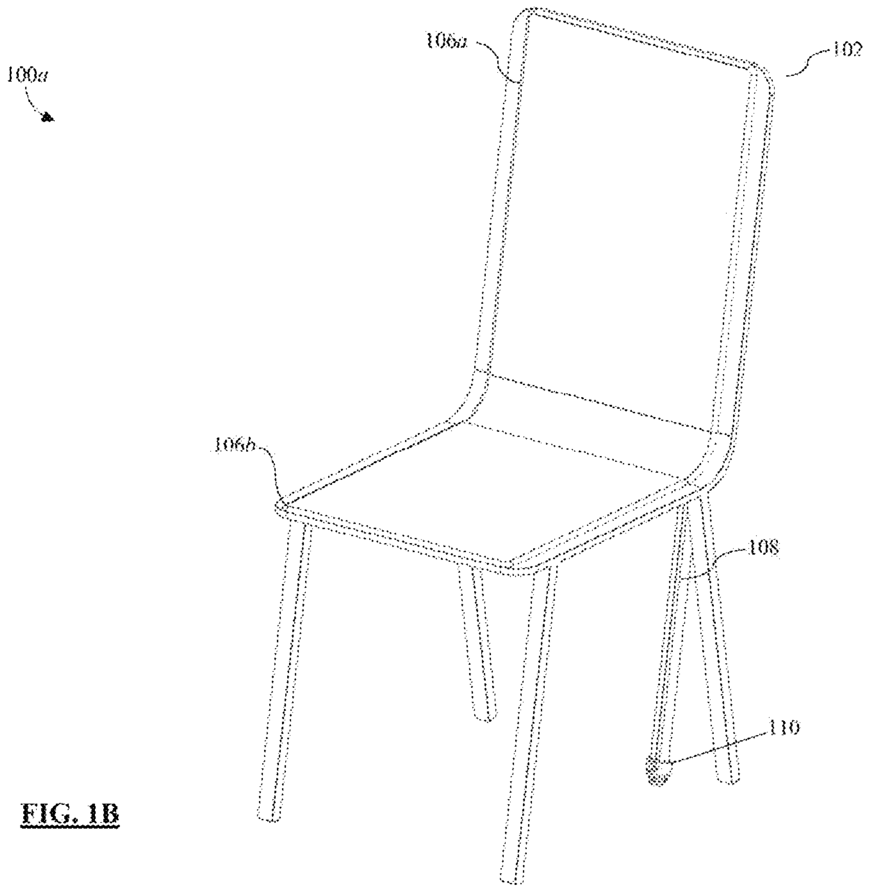
FIG. 1B is a perspective view of a personal heating and cooling apparatus, in accordance with certain aspects of the present disclosure.
Figure 1C:
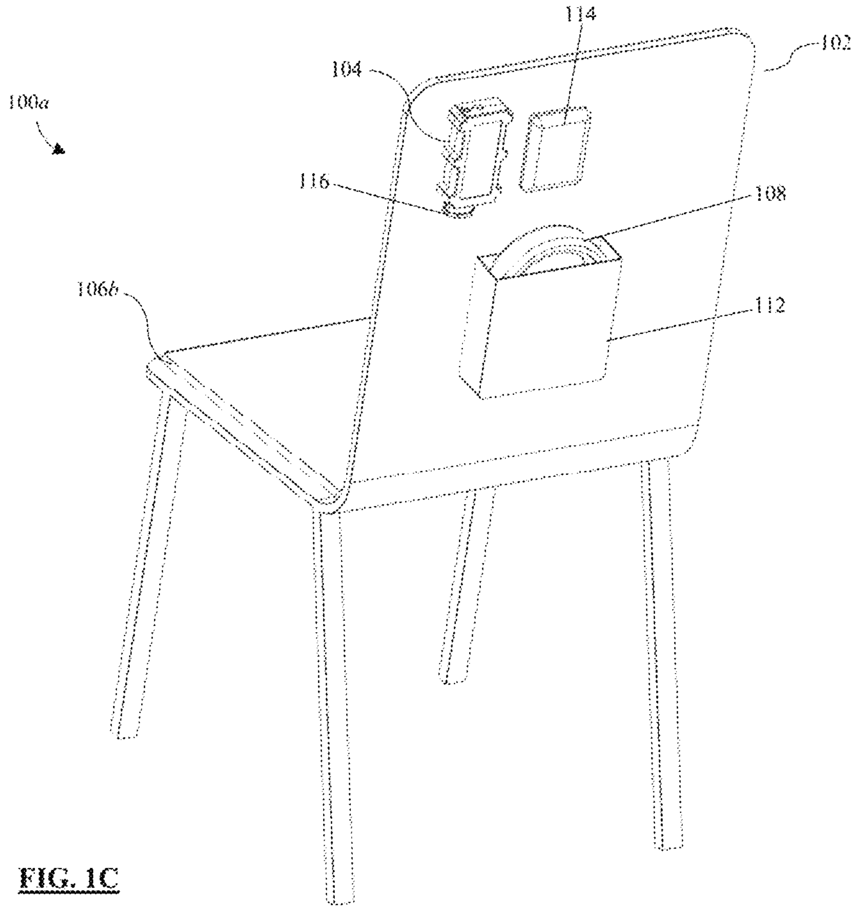
FIG. 1C is a perspective view of a personal heating and cooling apparatus, in accordance with certain aspects of the present disclosure.

Referring now to FIG. 1A, a perspective view of a personal heating and cooling system **100*a* is shown. In accordance with certain aspects of the present disclosure, system 100*a* may be comprised of a chair 102 having a plurality of heating and cooling elements operably engaged therewith. In certain embodiments, chair 102 may comprise a chair constructed of a foldable frame, such as a field chair, beach chair, lounger, camping chair, bench and the like. In certain embodiments, chair 102 may be embodied as one or more items of outdoor furniture, such as a deck chair, a dining chair, a bench, an outdoor sofa, an Adirondack chair, a chaise lounge and the like. In certain embodiments, chair 102 is configurable between a folded position and an open position. System 100*a* may comprise a pump assembly 104 coupled to a surface of chair 102 (e.g., a back surface). Pump assembly 104 may comprise a pump and a pump motor, as shown in more detail in FIG. 1D, below. System 100*a* may further comprise a trunk 108 comprising a supply line and a return line. In certain embodiments, trunk 108 may comprise an intake assembly 110 at a first end and a pump connector 116 at a second end. Pump connector 116 may be configured to establish a water-tight connection between the supply line of trunk 108 and a coolant intake line of pump assembly 104 and the return line of trunk 108 and a coolant output line of pump assembly 104. System 100*a* may further comprise an electronics assembly 114 mounted on a surface of chair 102 (e.g., the back surface). Electronics assembly 114 may comprise a controller comprising at least one processor and non-transitory computer readable medium comprising instructions stored thereon for commanding one or more operations of the at least one processor. In accordance with certain aspects of the present disclosure, the controller may be configured to command one or more operations of pump assembly 104 and one or more heating elements of system 100*a*. Electronics assembly 114 may comprise an exterior housing for retaining and protecting the elements of electronics assembly 114. Electronics assembly 114 may further comprise a battery pack configured to provide a flow of power to the controller, the pump motor and the one or more heating elements. In certain embodiments, electronics assembly 114 may comprise an interface for a power adapter to provide power to system 100*a* from a wall outlet. In certain embodiments, chair 102 may comprise a back pad 106*a* and a seat pad 106*b*, as shown in FIG. 1B. In certain embodiments, back pad 106*a* and a seat pad 106*b* may be removeable. In accordance with certain aspects of the present disclosure, back pad 106*a* and seat pad 106*b* may have at least one coolant line and at least one heating element contained therein; i.e., under a fabric surface of back pad 106*a* and seat pad 106*b* (as described in more detail below). Chair 102 may further comprise a trunk pocket 112 disposed on a back surface of chair 102. In accordance with certain embodiments, as shown in FIG. 1C, trunk 108 may be selectively disconnected from trunk connector 116 and placed in trunk pocket 112 for storage when system 100*a*** is not in use.

Figure 1D:
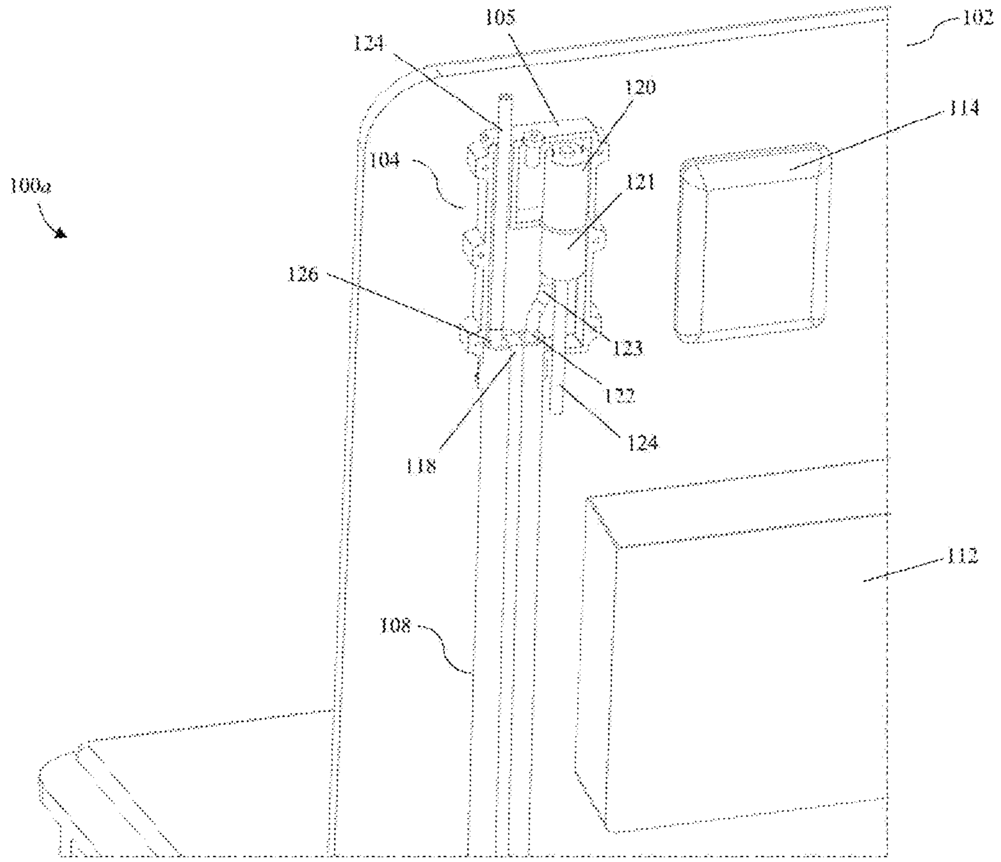
FIG. 1D is a perspective view of a personal heating and cooling apparatus, in accordance with certain aspects of the present disclosure.

Turning now to FIG. 1D, a more detailed component view of pump assembly 104 is shown. In accordance with certain aspects of the present disclosure, the components of pump assembly 104 may be housed in a pump housing 105. Pump assembly 104 may comprise a pump 121 and a pump motor 120 configured to circulate a volume of water from a supply line of trunk 108 through a length of flexible tubing 124 being disposed in an interior area of chair 102 and back through a return line of trunk 108. In certain embodiments, trunk 108 may comprise a return line 126 and a supply line 122 through which the volume of water is circulated. Trunk 108 may comprise a trunk jacket 118 constructed of neoprene or other thermally insulated material. Trunk jacket 118 may be constructed such that return line 126 and supply line 122 are separated by an area of material such that return line 126 and supply line 122 are thermally insulated from each other to prevent thermal transfer therebetween. Pump assembly 104 may comprise a coolant intake line 123 selectively engaged with supply line 122 and operably coupled to pump 121 to circulate a volume of water from supply line 122 through flexible tubing 124, through the interior area of chair 102, and back through return line 126 of trunk 108.

Figure 1E:
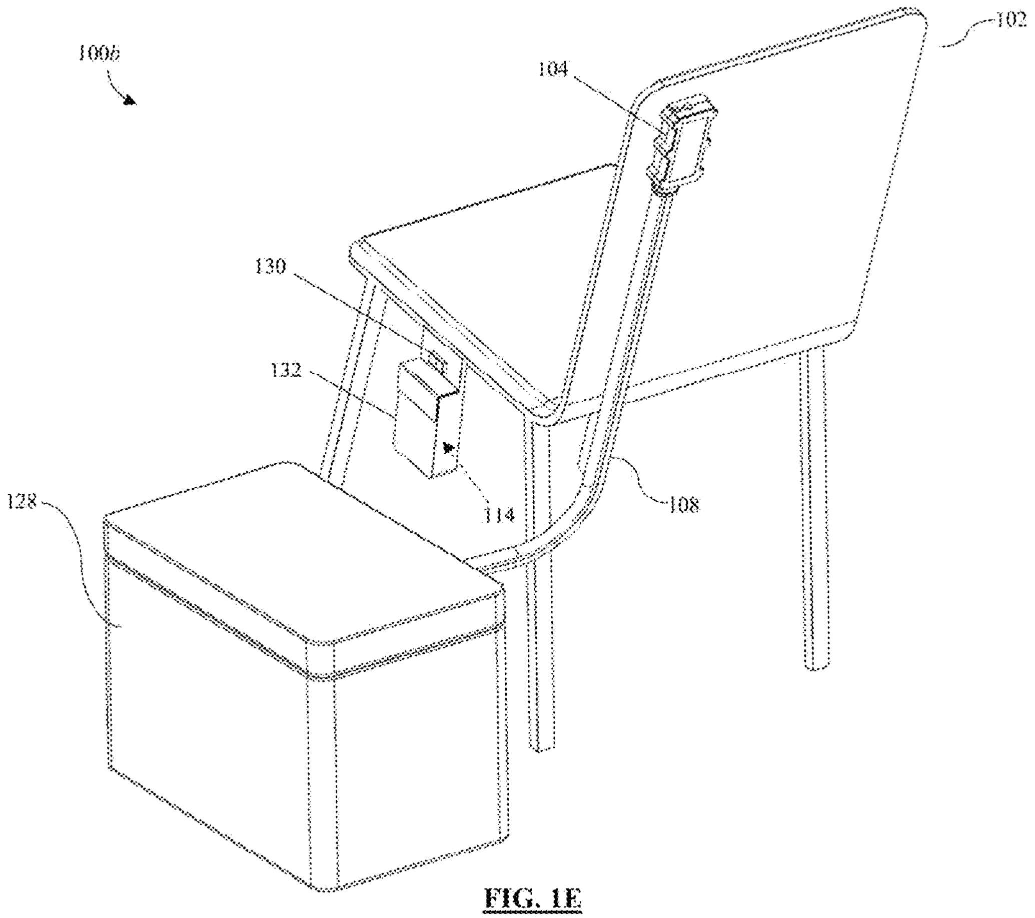
FIG. 1E is a perspective view of a personal heating and cooling system, in accordance with certain aspects of the present disclosure.
Figure 1F:
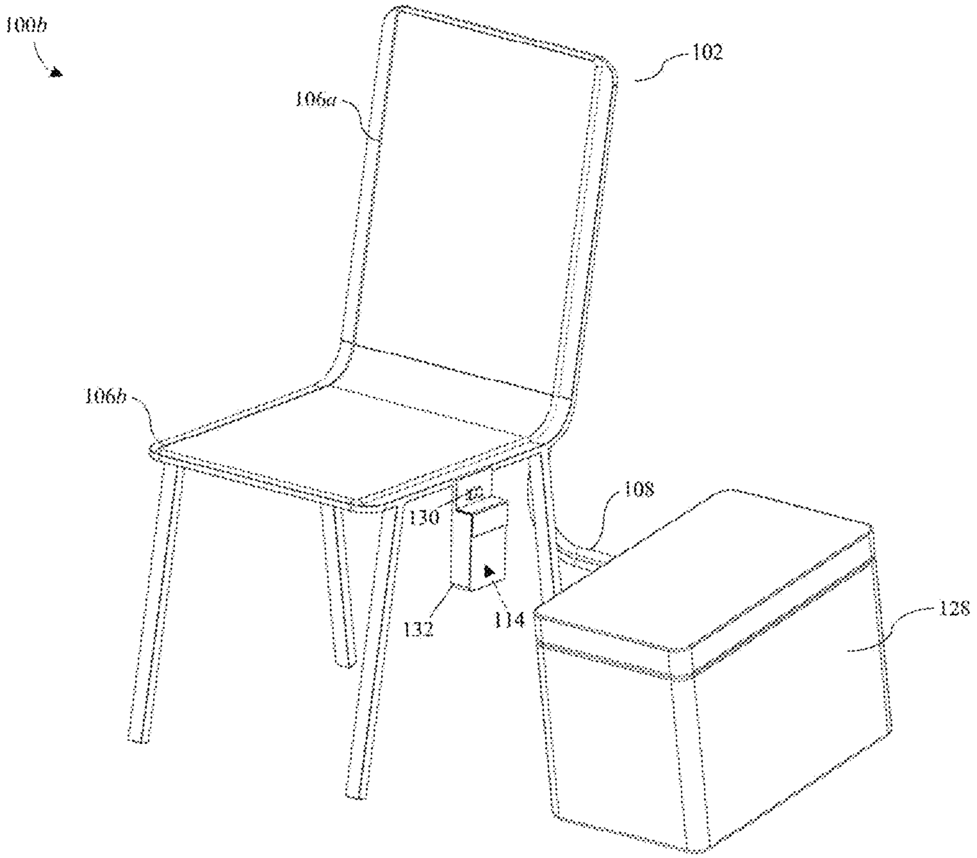
FIG. 1F is a perspective view of a personal heating and cooling system, in accordance with certain aspects of the present disclosure.

Turning now to FIGS. 1E-1F, a perspective view of a personal heating and cooling system 100*b* is shown. In accordance with certain aspects of the present disclosure, system 100*b* may comprise an alternative embodiment of system 100*a*. System 100*b* may comprise an electronics pocket 132 coupled to a surface of chair 102 in which electronics assembly 114 may be contained; e.g., as opposed to being mounted on the back of chair 102, as in system 100*a*. System 100*b* may comprise user interface controls 130 mounted on a surface of electronics pocket 132. User interface controls 130 may be configured to communicate a signal to the controller of electronics assembly 114 in response to an input from a user of system 100*b*; e.g., in response to a user pressing a button interface. The controller may be configured to command one or more heating or cooling functions of system 100*b* in response to the user input at user interface controls 130. In accordance with certain aspects of the present disclosure, the first end of trunk 108 may be interfaced with a thermal insulated cooler 128. Thermal insulated cooler 128 may comprise a volume of cold water (or other liquid) contained therein. The first end of trunk 108 may be placed inside an internal area of thermal insulated cooler 128 or may interface with a port or connector portion of thermal insulated cooler to circulate the volume of cold water contained therein to and from chair 102 via pump assembly 104. In accordance with certain aspects of the present disclosure, pump assembly 104 is operably engaged with a length of flexible tubing disposed in an interior area of back pad 106*a* and back pad 106*b* to circulate the volume of cold water therethrough in order to promote heat transfer between the volume of cold water and a user seated in chair 102.

Figure 1G:
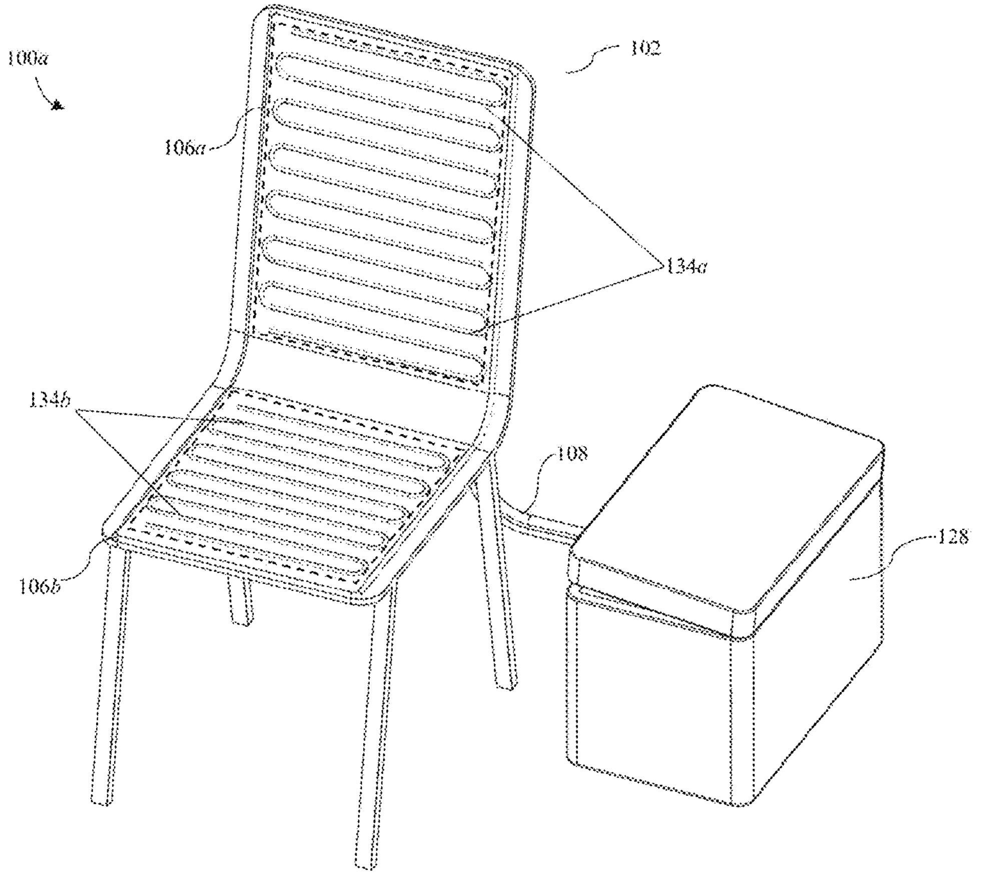
FIG. 1G is a perspective view of a personal heating and cooling system, in accordance with certain aspects of the present disclosure.
Figure 1H:
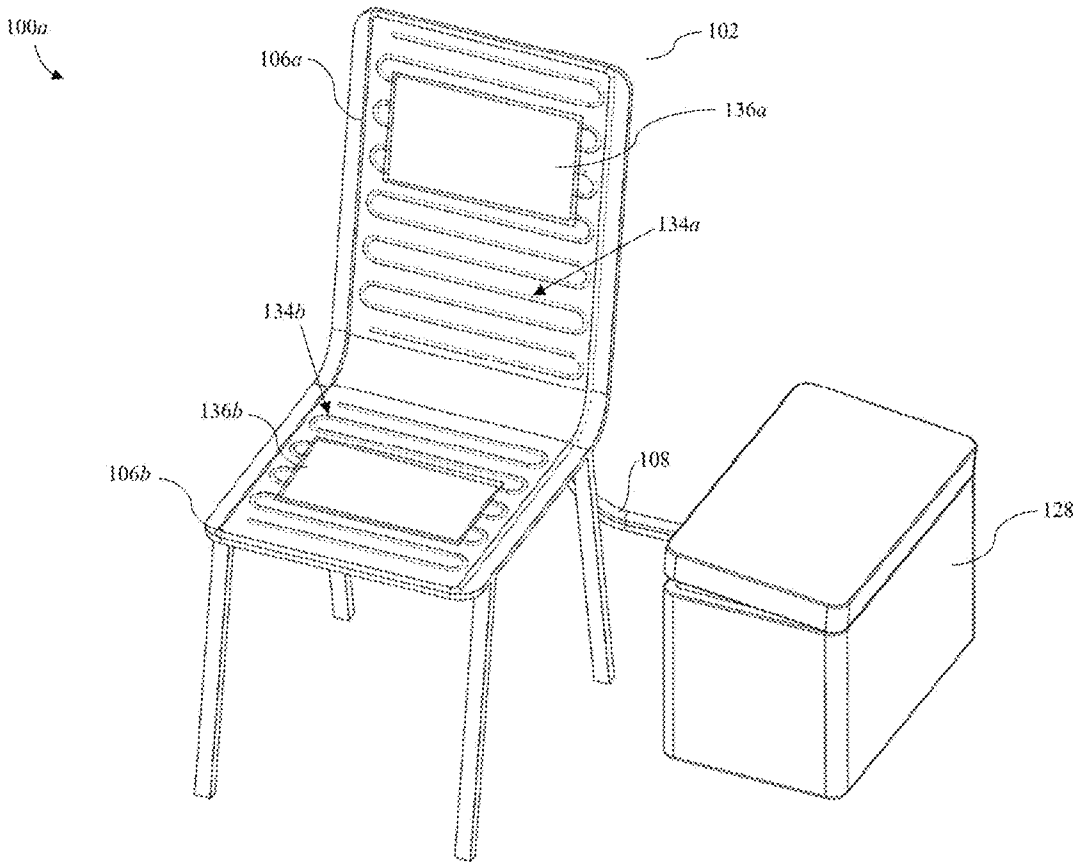
FIG. 1H is a perspective view of a personal heating and cooling system, in accordance with certain aspects of the present disclosure.

In accordance with certain embodiments, FIGS. 1G-1H depict chair 102 with an exterior surface of fabric of back pad 106*a* and seat pad 106*b* removed to expose the internal components of chair 102. As shown in more detail in FIGS. 1G and 1H, a first length of flexible tubing 134*a* may be routed across an internal area of back pad 106*a* and a second length of flexible tubing 134*b* may be routed across an internal area of seat pad 106*b*. In certain embodiments, first length of flexible tubing 134*a* and second length of flexible tubing 134*b* are vertically oriented such that the flexible tubing does not kink when chair 102 is configured in the folded position. As shown in FIG. 1H, in certain embodiments system 100*a* (and 100*b* as shown in FIGS. 1E and 1F) may comprise a first heating pad 136*a* disposed on the internal area of back pad 106*a*. In certain embodiments, first heating pad 136*a* may be disposed over a portion of the first length of flexible tubing 134*a*. In certain embodiments, system 100*a* (and/or 100*b* as shown in FIGS. 1E and 1F) may comprise a second heating pad 136*b* disposed on the internal area of seat pad 106*b*. In certain embodiments, second heating pad 136*b* is disposed over a portion of the second length of flexible tubing 134*b*. First heating pad 136*a* and second heating pad 136*b* may comprise one or more heating elements configured to produce a heating output in response to an electrical input. First heating pad 136*a* and second heating pad 136*b* may be operably engaged with electronics assembly 114 (as shown, e.g., in FIGS. 1A and 1E) to selectively deliver the heating output according to one or more operational modes.

Figure 2A:
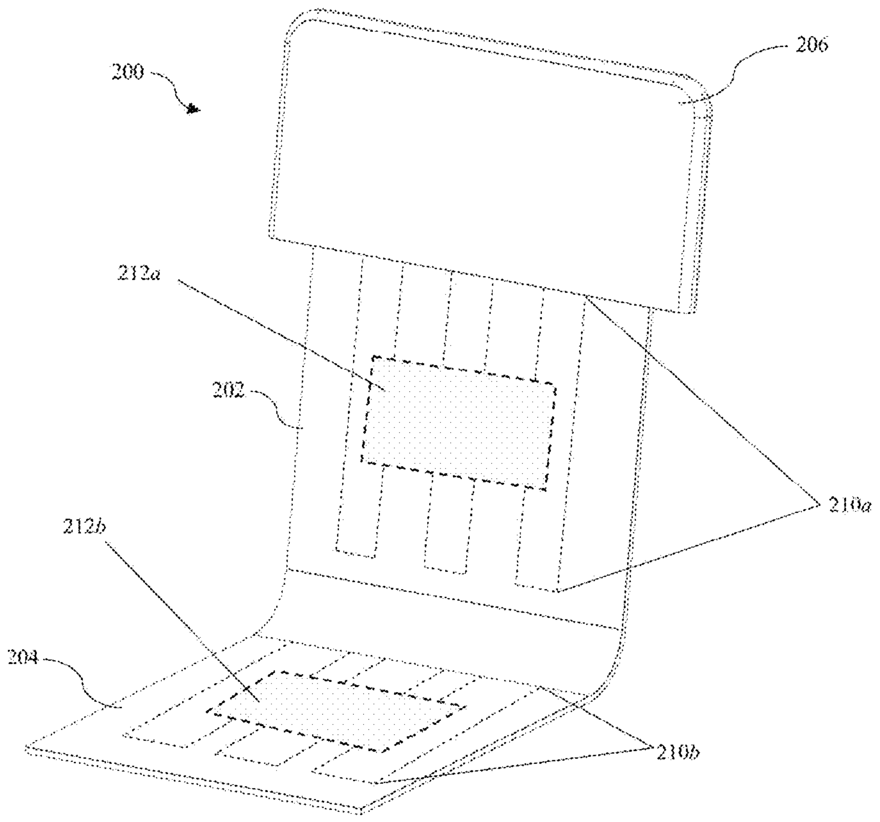
FIG. 2A is a perspective view of a personal heating and cooling apparatus, in accordance with certain aspects of the present disclosure.
Figure 2B:
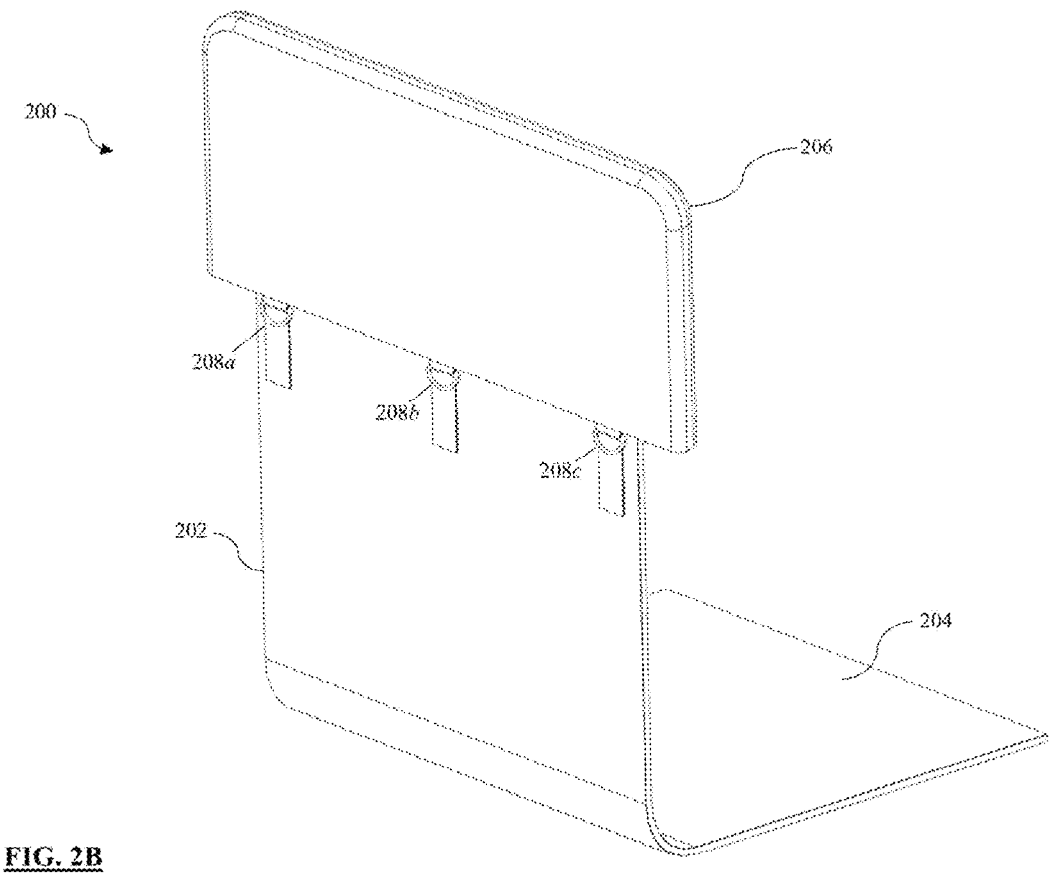
FIG. 2B is a perspective view of a personal heating and cooling apparatus, in accordance with certain aspects of the present disclosure.
Figure 4A:
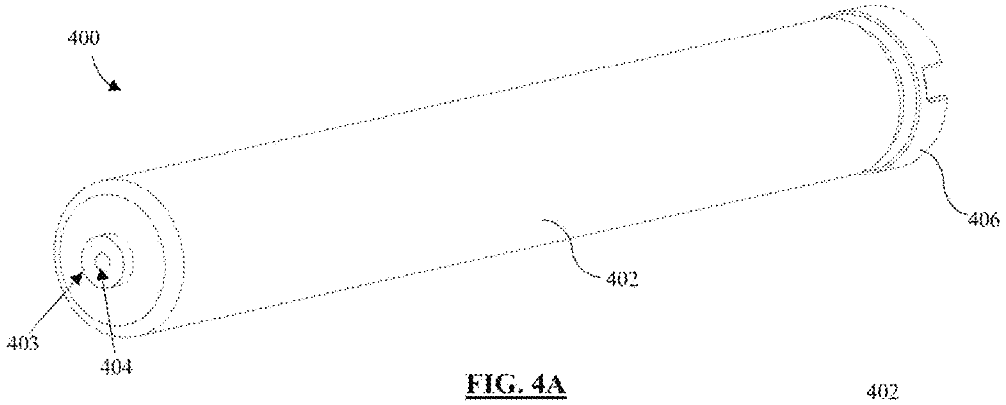
FIG. 4A is a perspective view of a pump for use in a personal heating and cooling apparatus and system, in accordance with certain aspects of the present disclosure.
Figure 4B:
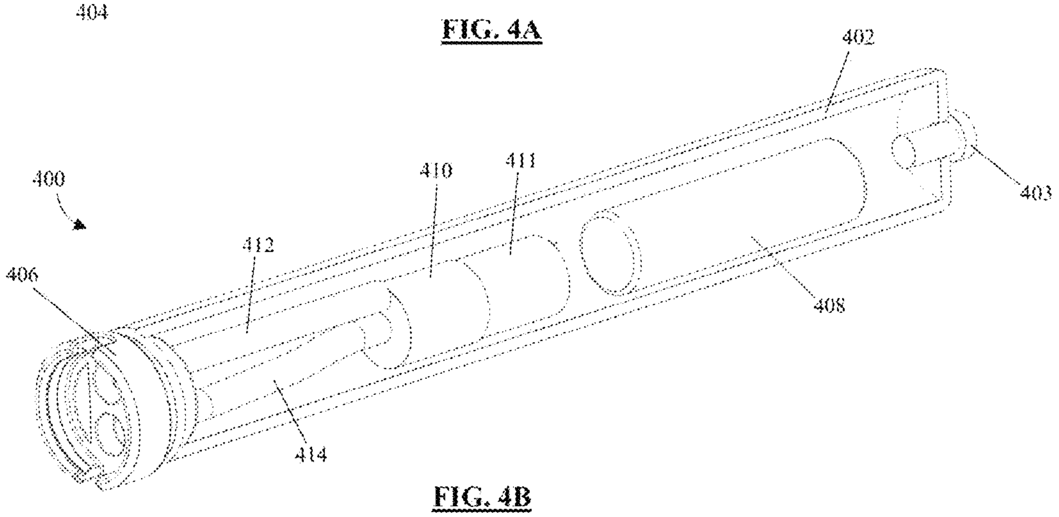
FIG. 4B is a cross-sectional view of a pump for use in a personal heating and cooling apparatus and system, in accordance with certain aspects of the present disclosure.

Referring now to FIGS. 2A-2B, perspective views of a removable chair pad 200, comprising an embodiment of the personal heating and cooling system of the present disclosure, are shown. In accordance with certain aspects of the present disclosure, removable chair pad 200 may be incorporated within system 100*a* and/or 100*b*, as shown in FIGS. 1A-1H. In accordance with certain aspects of the present disclosure, removable chair pad 200 may comprise a hood portion 206, a back portion 202 and a seat portion 204. Hood portion 206, back portion 202 and seat portion 204 may comprise a flexible outer fabric shell defining an exterior surface of hood portion 206, back portion 202 and seat portion 204. Hood portion 206, back portion 202 and seat portion 204 may comprise an insulative batting disposed in an interior area of hood portion 206, back portion 202 and seat portion 204 to serve as padding for removable chair pad 200 and increase comfort for a user. In accordance with certain aspects of the present disclosure, removable chair pad 200 may comprise a first length of flexible tubing 210*a* housed in the interior area of back portion 202. First length of flexible tubing 210*a* may be operably configured to circulate a volume of coolant therethrough. In accordance with certain aspects of the present disclosure, removable chair pad 200 may comprise a second length of flexible tubing 210*b* housed in the interior area of seat portion 204. Second length of flexible tubing 210*b* may be operably configured to circulate a volume of coolant therethrough. In accordance with certain aspects of the present disclosure, first length of flexible tubing 210*a* and/or second length of flexible tubing 210*b* may be operably engaged with at least one pump (e.g., pump 400 as shown in FIGS. 4A-4B) in order to circulate the volume of coolant. In certain embodiments, first length of flexible tubing 210*a* and/or second length of flexible tubing 210*b* may be constructed from one continuous length of tubing.

In accordance with certain aspects of the present disclosure, removable chair pad 200 may comprise a first heating pad 212*a* disposed on an interior area of back portion 202 and may comprise a second heating pad 212*b* disposed on an interior area of seat portion 204. In accordance with certain aspects of the present disclosure, first heating pad 212*a* and/or second heating pad 212*b* may be operably engaged with a controller and a power source (not shown in FIGS. 2A-2B) to produce a heating output at first heating pad 212*a* and/or second heating pad 212*b*. In accordance with certain aspects of the present disclosure, hood portion 206 may be configured to selectively interface with a back portion of an existing chair, such that removable chair pad 200 may be selectively secured to the existing chair for use as a personal heating and cooling system by a user. Hood portion 206 may comprise one or more connectors 208*a*-*c* configured to securely couple removable chair pad 200 to the existing chair. In accordance with certain embodiments, a bottom surface of removable chair pad 200 may comprise a non-slip fabric to increase friction and enhance contact between removable chair pad 200 and the existing chair, when selectively coupled. In accordance with certain embodiments, removable chair pad 200 may be reversible such that either exterior surface may be faced up when removable chair pad 200 is in use. In accordance with certain aspects of the present disclosure, removable chair pad 200 may be used in a flat configuration in which hood portion 206 is not engaged with a chair or other structure; for example, as a pad for a bench and/or as a pad on the ground (e.g., at the beach).

Figure 3A:
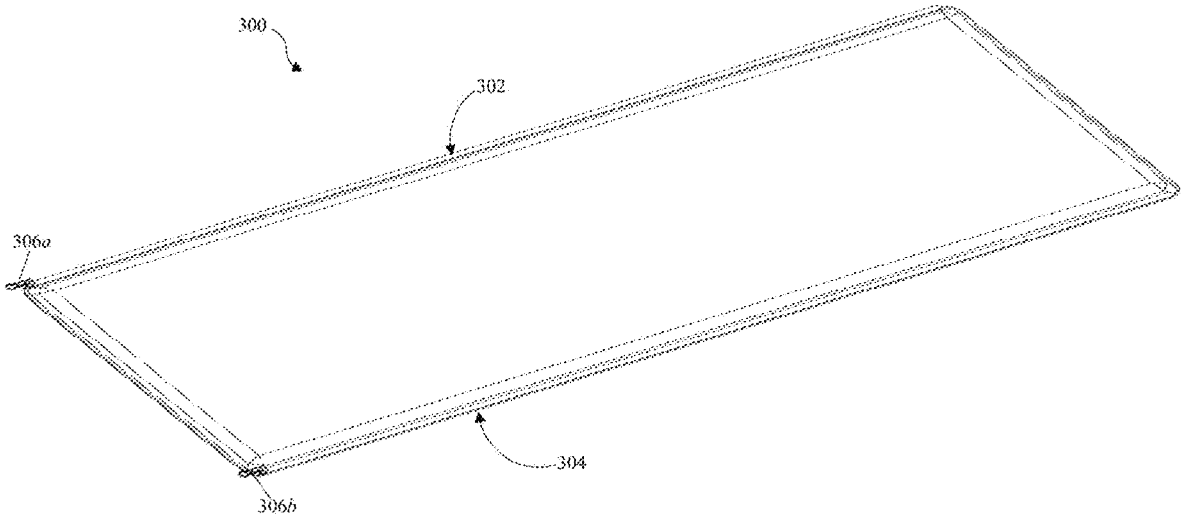
FIG. 3A is a perspective view of a personal heating and cooling apparatus, in accordance with certain aspects of the present disclosure.
Figure 3B:
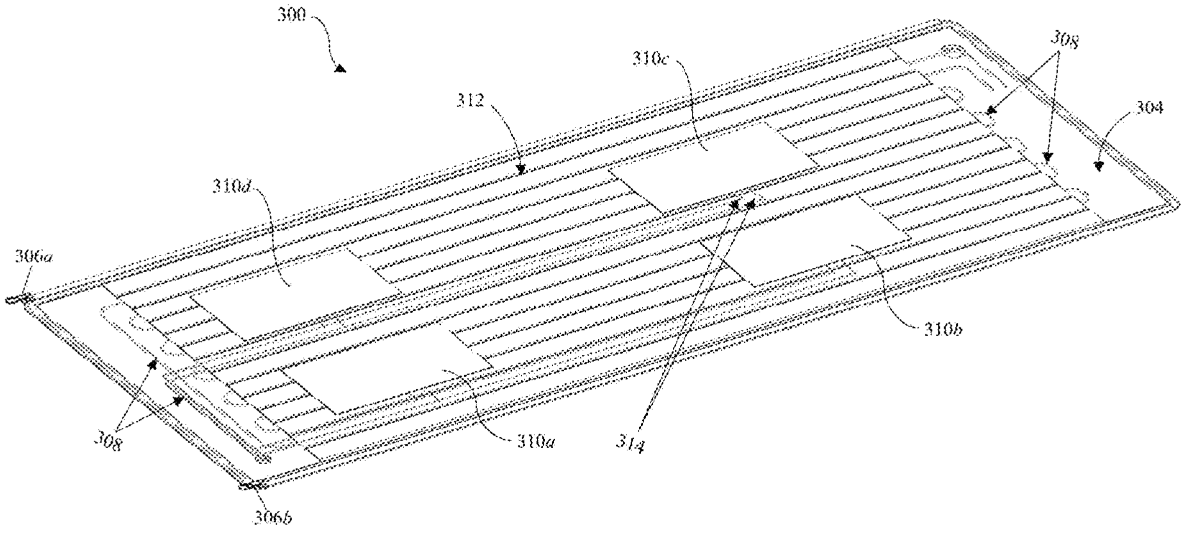
FIG. 3B is a perspective view of an assembly for a personal heating and cooling apparatus, in accordance with certain aspects of the present disclosure.
Figure 3C:
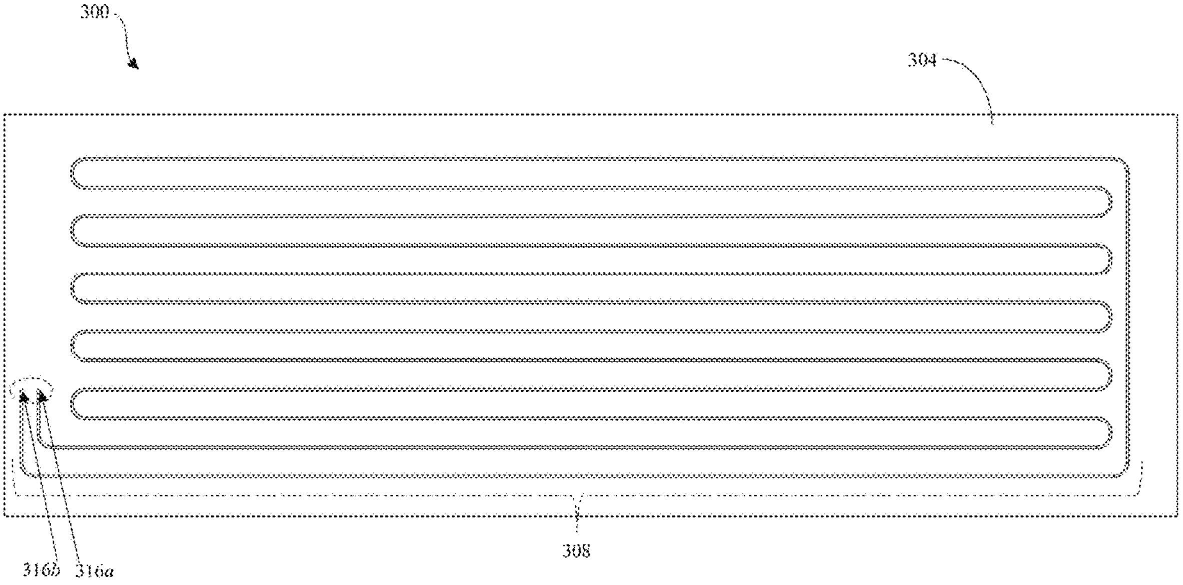
FIG. 3C is a plan view of a layout of a coolant line for a personal heating and cooling apparatus, in accordance with certain aspects of the present disclosure.

Referring now to FIGS. 3A-3C, various views of a personal heating and cooling apparatus 300 are shown. In accordance with certain aspects of the present disclosure, FIG. 3A is a perspective view of apparatus 300 configured in a flat position/configuration. In accordance with certain embodiments, apparatus 300 comprises an upper fabric surface 302 and a lower fabric surface 304. Upper fabric surface 302 and lower fabric surface 304 are coupled together to comprise an exterior shell of apparatus 300. In certain embodiments, apparatus 300 may comprise a first connector 306*a* and a second connector 306*b* coupled to a first corner and a second corner of apparatus 300; e.g., along a short side of apparatus 300. First connector 306*a* and second connector 306*b* may be configured to selectively secure apparatus 300 to one or more attachment points of another seating apparatus (e.g., a chair, a bench, a hunting stand, a golf cart seat, etc.).

Referring now to FIG. 3B, a perspective view of apparatus 300 with upper fabric surface 302 removed to expose the internal components of apparatus 300 is shown. In accordance with certain aspects of the present disclosure, apparatus 300 may comprise a length of flexible plastic tubing 308 disposed on an interior area of lower fabric surface 304. In accordance with certain embodiments, flexible plastic tubing 308 may comprise a 1/16" internal diameter and 1/8" outer diameter tubing. In certain embodiments, flexible plastic tubing 308 may be constructed of a mildew-resistant plastic. Flexible plastic tubing 308 may be oriented in straight lines on the interior area of lower fabric surface 304 in order to form a plurality of evenly spaced, parallel rows. A mesh fabric 312 may be sewn or otherwise coupled to the interior area of lower fabric surface 304 to retain flexible plastic tubing 308 in place. Mesh fabric 312 may be stitched to the interior area of lower fabric surface 304 along the spacing between the plurality of evenly spaced, parallel rows of flexible plastic tubing 308 to form a plurality of retaining areas to retain flexible plastic tubing 308 in place. In certain embodiments, apparatus may comprise a length of insulative batting disposed on the interior area of lower fabric surface 304. The insulative batting may comprise a plurality of channels being cut or otherwise formed therein, in which the length of flexible plastic tubing 308 may be positioned in order to form the plurality of evenly spaced, parallel rows. Mesh fabric 312 may be stitched or otherwise coupled to the insulative batting to secure flexible plastic tubing 308 to the insulative batting. In accordance with certain aspects of the present disclosure, apparatus 300 may comprise one or more heating pads 310*a-d*. Heating pads 310*a-d* may be coupled (e.g., sewn) to a surface of mesh fabric 312. One or more conductive wires 314 may be operably engaged with one or more heating elements of heating pads 310*a-d* in order to provide a flow of electricity from at least one power source to the one or more heating elements of heating pads 310*a-d*.

Referring now to FIG. 3C, a top-down plan view of flexible plastic tubing 308 disposed on the interior area of lower fabric surface 304 is shown. In accordance with certain aspects of the present disclosure, flexible plastic tubing 308 extends from a first end 316*a* to a second end 316*b*. First end 316*a* may comprise a coolant inlet and be operably engaged with a pump (e.g., pump 400 of FIGS. 4A-4B) to receive a volume of coolant therethrough. Second end 316*b* may comprise a coolant outlet and may be operably engaged with a return line of a trunk to circulate the volume of coolant therethrough. As shown in FIG. 3C, flexible plastic tubing 308 may be disposed on the interior area of lower fabric surface 304 in evenly spaced, parallel rows between a first end of lower fabric surface 304 and a second end of lower fabric surface 304. In accordance with certain aspects of the present disclosure, flexible plastic tubing 308 is oriented in such a way as to prevent/minimize bending or kinking of flexible plastic tubing 308 when apparatus 300 is in use and/or interfaced with a seating apparatus (e.g., a chair, a bench, a hunting stand, a golf cart seat, etc.).

Referring now to FIGS. 4A-4B, perspective and cross-sectional views of a pump assembly 400 for use in a personal heating and cooling apparatus and system are shown. In certain embodiments, pump assembly 400 may comprise an embodiment of pump assembly 104, as shown in FIGS. 1A-1F. In accordance with certain aspects of the present disclosure, pump assembly 400 may be operably engaged with removable chair pad 200 (as shown in FIGS. 2A-2B) to circulate a volume of coolant through first length of flexible tubing 210*a* and/or second length of flexible tubing 210*b* (as shown in FIGS. 2A-2B). In accordance with certain aspects of the present disclosure, pump assembly 400 may be operably engaged with personal heating and cooling apparatus 300 (as shown in FIG. 3) to circulate a volume of coolant through flexible plastic tubing 308 (as shown in FIG. 3). As shown in FIGS. 4A-4B, pump assembly 400 may comprise a pump housing 402. Pump housing 402 may be substantially cylindrical in shape and be configured to fit into a pocket or pouch of a portable heating and cooling apparatus for storage and operation. Pump assembly 400 may comprise a switch 403 and charging port 404 disposed at a distal end of pump assembly 400 and may comprise a coupler 406 disposed at a proximal end of pump assembly 400. Switch 403 may be configured to enable a user to operably engage and disengage pump assembly 400 by engaging switch 403 to an ON/OFF position. Charging port 404 may be configured to receive an electrical contact of a charging cable in order to provide a charge to rechargeable battery 408. Pump assembly 400 may comprise a pump 410 and a pump motor 411. Pump 410 may comprise a positive displacement pump, such as a diaphragm pump, membrane pump, piston pump, plunger pump, and the like. Pump motor 411 may be operably configured to actuate pump 410. In certain embodiments, pump motor 411 may comprise a voltage in the range of 3V to 12V. Pump assembly 400 may further comprise a rechargeable battery 408 configured to provide a flow of power to pump motor 411. Pump 410 may be operably engaged with a coolant inlet 412 to receive and circulate a volume of coolant therefrom. Pump assembly 400 may further comprise a coolant outlet 414 to circulate the volume of coolant received at the coolant inlet 412. Coolant inlet 412 and coolant outlet 414 may be connected to a first port and a second port of couper 406. Coupler 406 may be configured to establish a water-tight connection between a coolant supply line and a coolant return line of a trunk (e.g., trunk 108 as shown in FIGS. 1A-1F).

Figure 5:
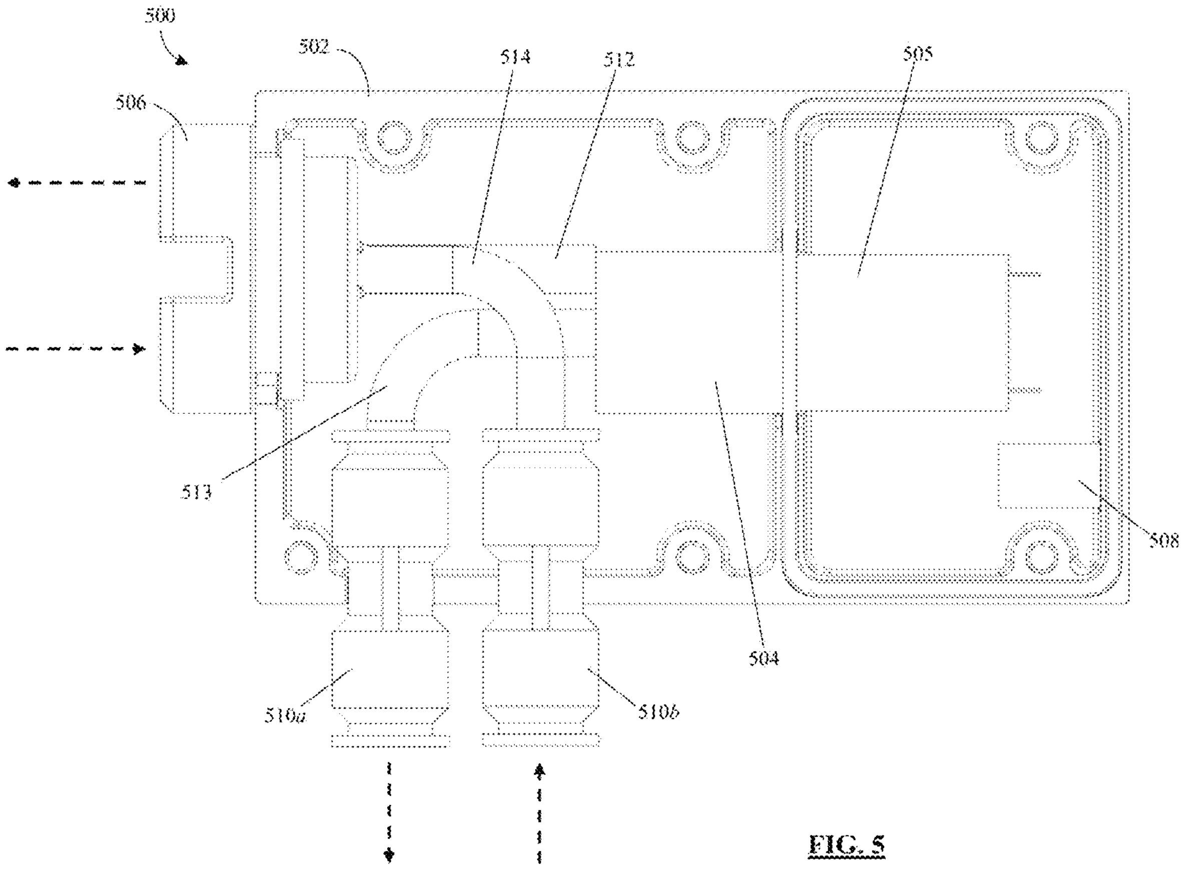
FIG. 5 is a cross-sectional view of a pump for use in a personal heating and cooling apparatus and system, in accordance with certain aspects of the present disclosure.

Referring now to FIG. 5, a cross-sectional view of a pump assembly 500 for use in a personal heating and cooling apparatus and system is shown. In accordance with certain aspects of the present disclosure, pump assembly 500 may be embodied as pump assembly 104, as shown in FIGS. 1A-1F. In accordance with certain aspects of the present disclosure, pump assembly 500 may comprise a pump housing 502 configured to securely house the internal components of pump assembly 500. A coupler 506 is disposed on a first end of pump housing 502. In accordance with certain embodiments, coupler 506 is configured to selectively establish a selective (i.e., removeable) water-tight connection between a supply line and a return line of a trunk (e.g., trunk 108 in FIGS. 1A-1H) and a coolant inlet 512 and a coolant return line 514 of pump assembly 500. Pump assembly 500 may further comprise a power supply port 508 operably engaged with a pump motor 505 to provide an electrical power supply from a power source pump motor 505. Pump motor 505 may be operably engaged with pump 504 to circulate a volume of coolant from coolant inlet 512, through coolant supply line 513 to coolant return line 514. Pump 504 may comprise a positive displacement pump, such as a diaphragm pump, membrane pump, piston pump, plunger pump, and the like. Pump assembly 500 may further comprise a first tube connector 510*a* and a second tube connector 510*b*. First tube connector 510*a* may be operably coupled to an end of coolant supply line 513 to receive a volume of coolant therethrough. Second tube connector 510*b* may be operably coupled to an end of coolant return line 514 to pass a volume of coolant therethrough. In accordance with certain aspects of the present disclosure, first tube connector 510*a* and second tube connector 510*b* are configured to establish a selective (i.e., removeable) water-tight connection between pump assembly 502 and a first end and a second end of a flexible coolant tube, respectively, of a personal heating and cooling apparatus (e.g., flexible plastic tubing 308 of apparatus 300, as shown in FIGS. 3A-3C).

In accordance with certain aspects of the present disclosure, pump assembly 500 is configured to selectively establish a water-tight connection between a trunk comprising a coolant supply line and a coolant return line and connector 506. Pump motor 505 is operably engaged with pump 504 to pump a volume of coolant from a reservoir, in which a second end of the trunk is positioned, through coolant inlet 512 and to the coolant supply line 513. Coolant supply line 513 is securely coupled to first tube connector 510*a*. A first end of a flexible coolant tube of a personal cooling apparatus is selectively coupled to first tube connector 510*a* to establish a water-tight connection. First tube connector 510*a* is configured to enable a flow of coolant between coolant supply line 513 and the first end of the flexible coolant tube. In accordance with certain aspects of the present disclosure, a volume of coolant is circulated through the length of the flexible coolant tube (e.g., through an interior area of a chair in which the flexible coolant tube is installed) from the first end to a second end via the pressure produced by pump 504. The second end of the flexible coolant tube may be selectively coupled to second tube connector 510*b* to establish a water-tight connection. The circulated volume of coolant is directed through second tube connector 510*b* to coolant return line 514 and out of the pump assembly 500 to the coolant return line of the trunk. In accordance with certain aspects of the present disclosure, pump assembly 500 is configured to be selectively connected and disconnect from the trunk via coupler 506 and selectively connected and disconnect from the first end and the second end of the flexible coolant tube via first tube connector 510*a* and second tube connector 510*b*.

Figure 6A:
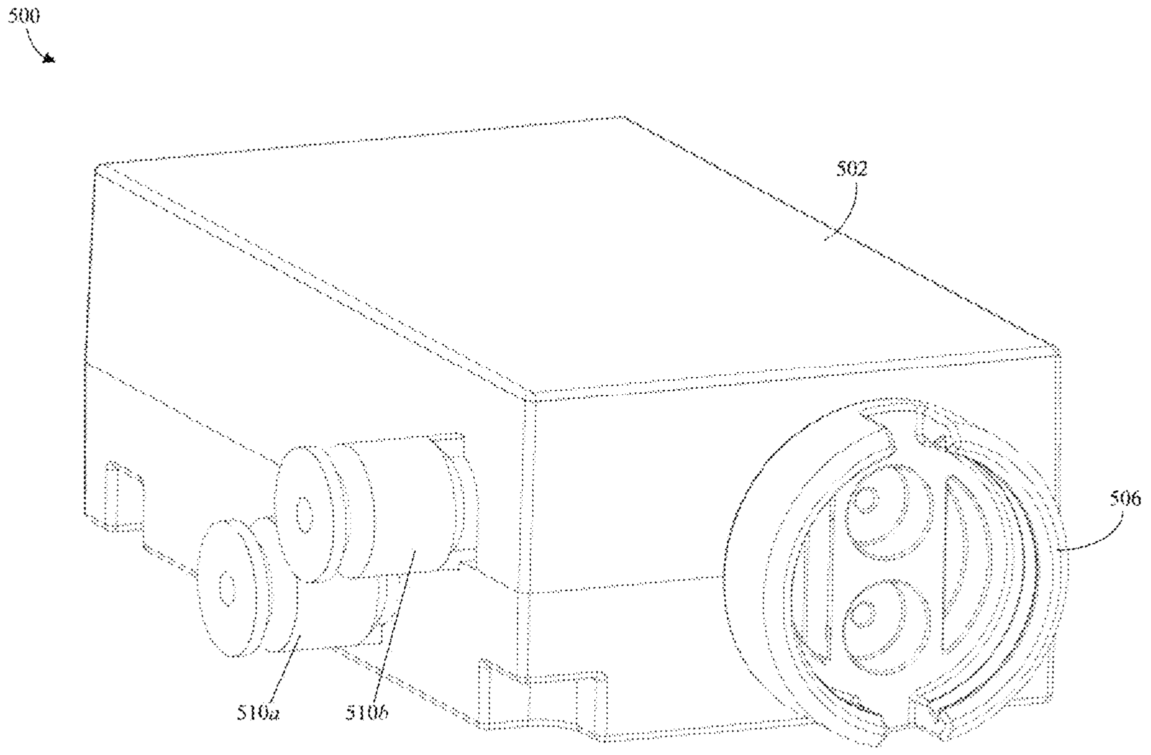
FIG. 6A is a perspective view of a pump for use in a personal heating and cooling apparatus and system, in accordance with certain aspects of the present disclosure.
Figure 6B:
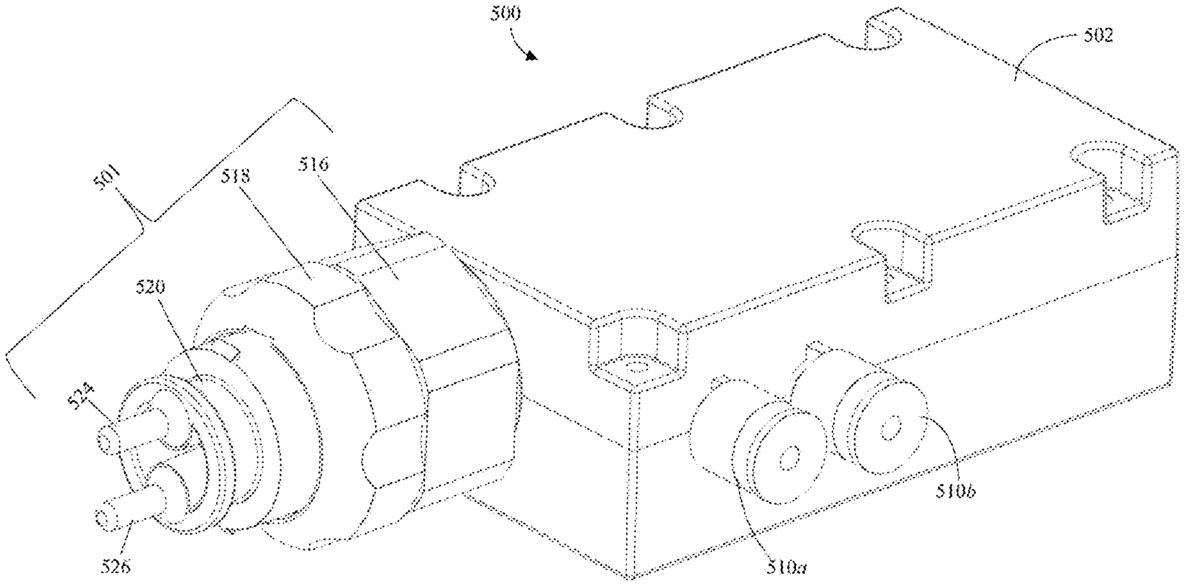
FIG. 6B is a perspective view of a pump for use in a personal heating and cooling apparatus and system, in accordance with certain aspects of the present disclosure.
Figure 7A:
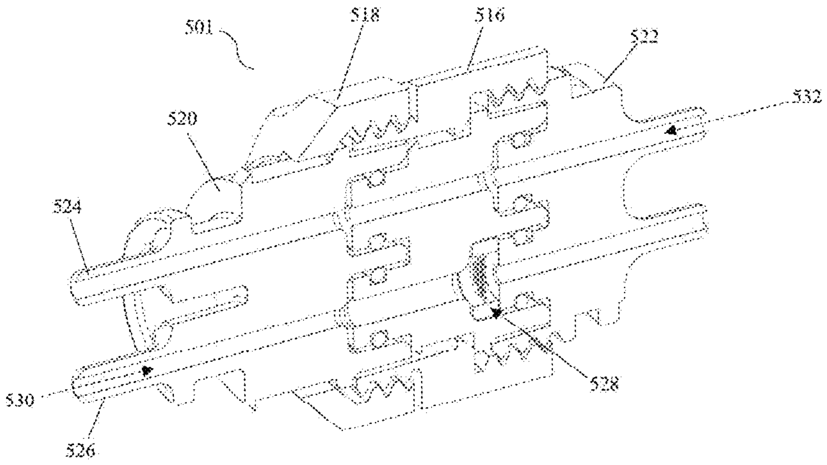
FIG. 7A is a cross-sectional view of a connector and filter assembly for use in a personal heating and cooling apparatus and system, in accordance with certain aspects of the present disclosure.
Figure 7B:
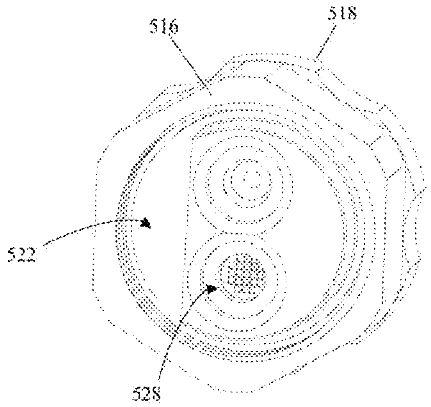
FIG. 7B is a perspective view of a connector and filter assembly for use in a personal heating and cooling apparatus and system, in accordance with certain aspects of the present disclosure.

Referring now to FIGS. 6A-6B, perspective views of pump assembly 500 are shown. In accordance with certain aspects of the present disclosure, FIG. 6A illustrates an illustrative form factor of pump housing 502, coupler 506 and first tube connector 510*a* and second tube connector 510*b*. FIG. 6B depicts a perspective view of a trunk connector assembly 501 coupled to coupler 506 of pump assembly 500. In accordance with certain aspects of the present disclosure, trunk connector assembly 501 is configured to enable a selective, water-tight connection between a trunk (e.g., trunk 108 of FIGS. 1A-1H) and pump assembly 500. In accordance with certain embodiments, trunk connector assembly 501 may comprise a connector attachment 516, a threaded collar 518 and a trunk connector 520. Referring now also to FIGS. 7A-7B, trunk connector assembly 501 may further comprise a pump connector 522. In accordance with certain embodiments, pump connector 522 may comprise a first elongated stem and a second elongated step configured to interface with coolant inlet 512 and coolant return line 514 (as shown in FIG. 5). Connector attachment 516 may be selectively coupled to pump connector 522 and may comprise a threaded portion configured to retain the interface between pump connector 522 the coolant inlet 512 and coolant return line 514 (as shown in FIG. 5). Trunk connector 520 may be selectively interfaced with connector attachment 516 and threaded collar 518 may be configured to secure trunk connector 520 to connector attachment 516 via a threaded mechanical interface. Trunk connector 520 may further comprise a supply line stem 526 and a return line stem 524 configured to interface with a supply line and a return line of the trunk. Trunk connector assembly 501 may further comprise a supply channel 530 extending through the length of trunk connector assembly 501 from supply line stem 526 to the first elongated stem of pump connector 522; and trunk connector assembly 501 may comprise a return channel 532 extending through the length of trunk connector assembly 501 from the second elongated stem of pump connector 522 to return line stem 524. Trunk connector assembly 501 may further comprise a filter 528 being positioned in an aperture between pump connector 522 and connector attachment 516. Filter 528 may comprise a filter screen configured to remove any particulate matter that is larger than the size of the filter mesh. In accordance with certain embodiments, trunk connector assembly 501 is configured to be disassembled to enable cleaning and replacement of filter 528.

Figure 8A:
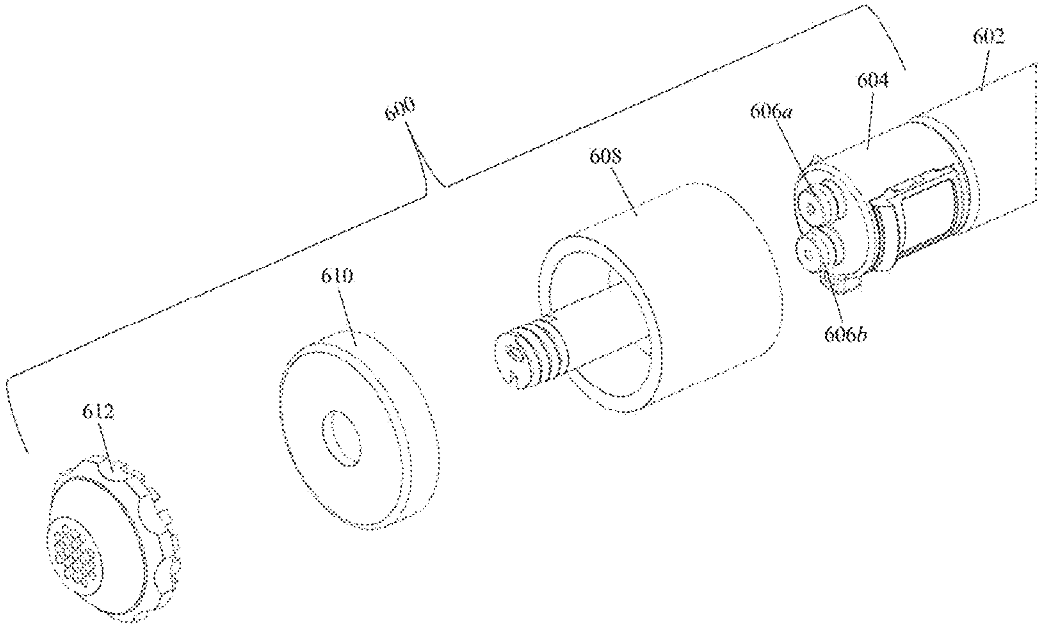
FIG. 8A is an exploded view of a filter assembly for a trunk line of a personal heating and cooling apparatus and system, in accordance with certain aspects of the present disclosure.
Figure 8B:
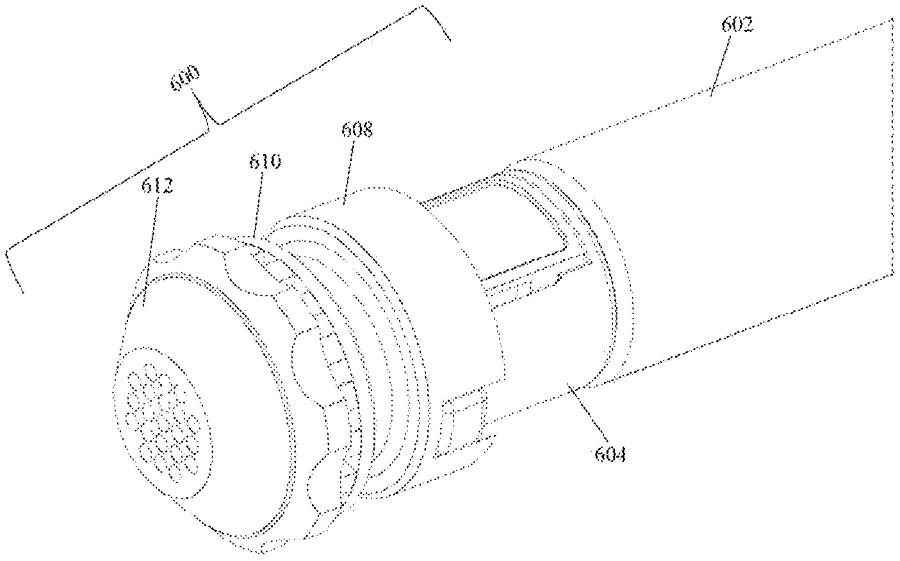
FIG. 8B is a perspective view of a filter assembly for a trunk line of a personal heating and cooling apparatus and system, in accordance with certain aspects of the present disclosure.

Referring now to FIGS. 8A-8B, an exploded view and a perspective view of an intake assembly 600 for a trunk 602 of a personal heating and cooling apparatus and system are shown. In accordance with certain aspects of the present disclosure, trunk 602 may comprise an embodiment of trunk 108, as shown in FIGS. 1A-1H; and intake assembly 600 may comprise an embodiment of intake assembly 110, as shown in FIGS. 1A-1B. In accordance with certain aspects of the present disclosure, intake assembly 600 may comprise a trunk fitting 604 coupled to a distal end of trunk 602. Trunk fitting 604 may comprise a supply line fitting 606*a* and a return line fitting 606*b* being operably interfaced with a supply line and a return line, respectively, of trunk 602. Intake assembly 600 may further comprise an intake stem 608 configured to be securely interfaced with trunk fitting 604. Intake assembly 600 may further comprise an intake cap 610 configured to be coupled to intake stem 608 and an intake filter 612 configured to be securely interfaced with intake stem 608 and intake cap 610. When intake assembly 600 is fully assembled, as shown in FIG. 8B, trunk 602 is configured to be submerged in a volume of coolant (i.e., cold water) contained in a reservoir (i.e., a thermal insulated cooler). The volume of coolant is circulated through intake assembly 600 to trunk 602 via mechanical action of a connected pump (e.g., as described above).

Figure 9A:
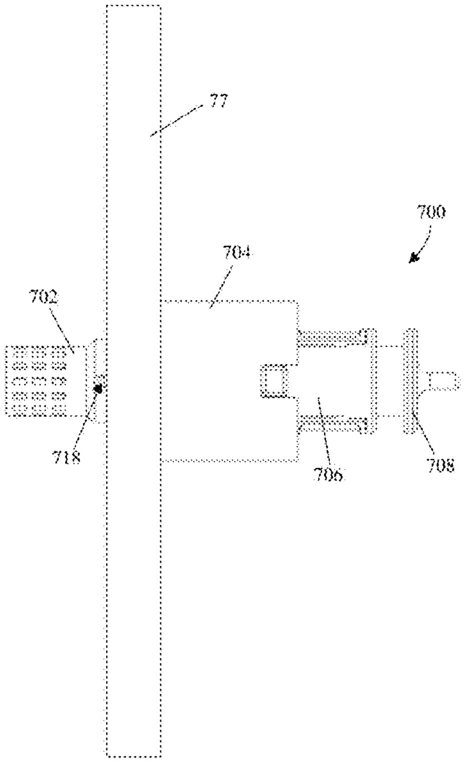
FIG. 9A is a plan view of a drain plug adapter for use in a personal heating and cooling system, in accordance with certain aspects of the present disclosure.
Figure 9B:
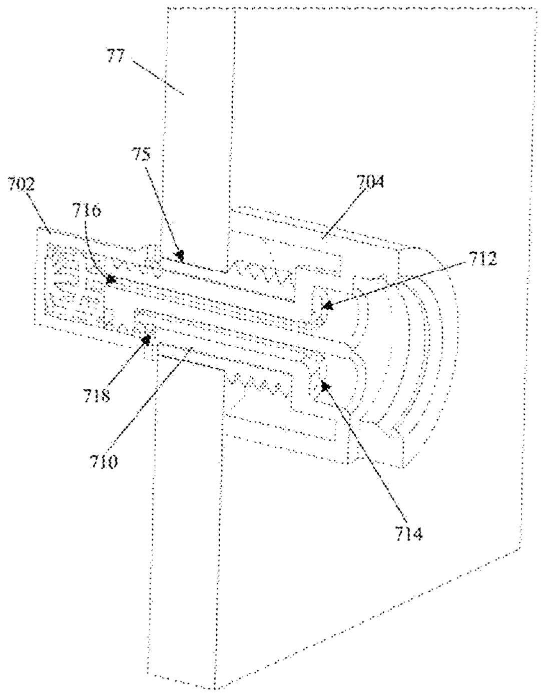
FIG. 9B is a cross-sectional view of a drain plug adapter for use in a personal heating and cooling system, in accordance with certain aspects of the present disclosure.

Referring now to FIGS. 9A-9B, a plan view and a cross-sectional view of a drain plug adapter assembly 700 for use in a personal heating and cooling system are shown. In accordance with certain aspects of the present disclosure, drain plug adapter assembly 700 is configured to enable a personal heating and cooling system (e.g., system 100*a,b* as shown in FIGS. 1A-1H) to circulate a volume of coolant (e.g., water) to and from a thermal insulated cooler 77 via drain port 75. In accordance with certain aspects of the present disclosure, drain plug adapter assembly 700 is configured to interface with drain port 75 of thermal insulated cooler 77, as shown in FIGS. 9A-9B. In accordance with certain aspects of the present disclosure, drain plug adapter assembly 700 comprises a drain plug adapter 704 configured to interface with an outer wall of thermal insulated cooler 77. Drain plug adapter 704 may comprise a stem portion 710 configured to extend through drain port 75 to an internal area of thermal insulated cooler 77. Drain plug adapter assembly 700 may comprise a filter basket 702 configured to be securely interfaced with a threaded end of stem portion 710. The interface between filter basket 702 the threaded end of stem portion 710 may be configured to retain drain plug adapter assembly 700 in place on drain port 75. In accordance with certain embodiments, drain plug adapter 704 may comprise a supply line aperture 712 and a return line aperture 714. Drain plug adapter 704 may further comprise a supply channel 716 extending from a distal end of stem portion 710 to supply line aperture 712. Drain plug adapter 704 may further comprise a return channel 716 extending from a return port 718 disposed on a lateral portion of stem portion 710 to return line aperture 714. In accordance with certain embodiments, drain plug adapter assembly 700 may further comprise a trunk adapter 706 and a trunk connector 708 configured to establish a water-tight connection between drain plug adapter assembly 700 and a trunk (e.g., trunk 108 as shown in FIGS. 1A-1H). In accordance with certain aspects of the present disclosure, drain plug adapter assembly 700 is configured to establish a water-tight connection between supply line aperture 712 and a supply line of the trunk and return line aperture 714 and a return line of the trunk. In accordance with certain aspects of the present disclosure, a user may disconnect drain plug adapter assembly 700 from thermal insulated cooler 77 by unscrewing filter cap 702 from stem portion 710 and removing stem portion 710 from drain port 75.

Figure 10:
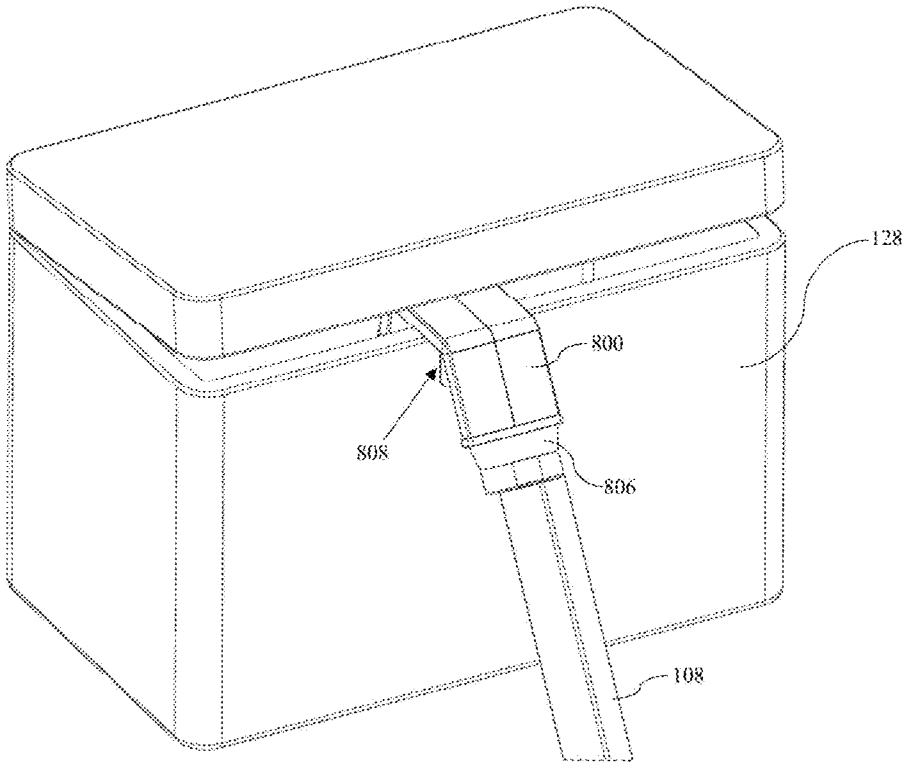
FIG. 10 is a functional perspective view of a tube bridge connector operably interfaced with a thermal insulated cooler for use in a personal heating and cooling system, in accordance with certain aspects of the present disclosure.
Figure 11A:
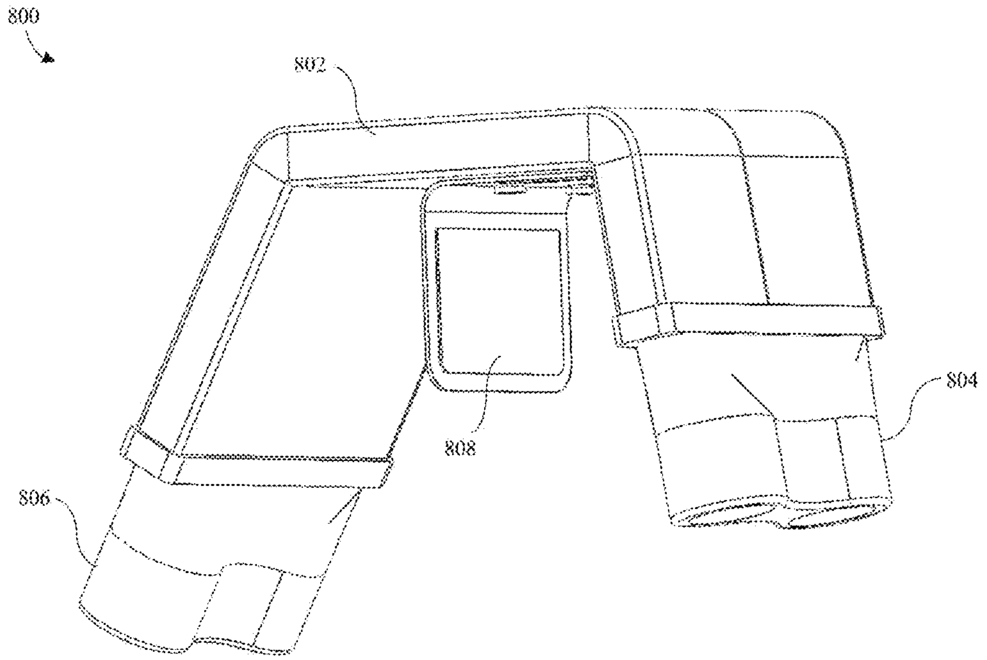
FIG. 11A is a perspective view of a tube bridge connector for use in a personal heating and cooling system, in accordance with certain aspects of the present disclosure.
Figure 11B:
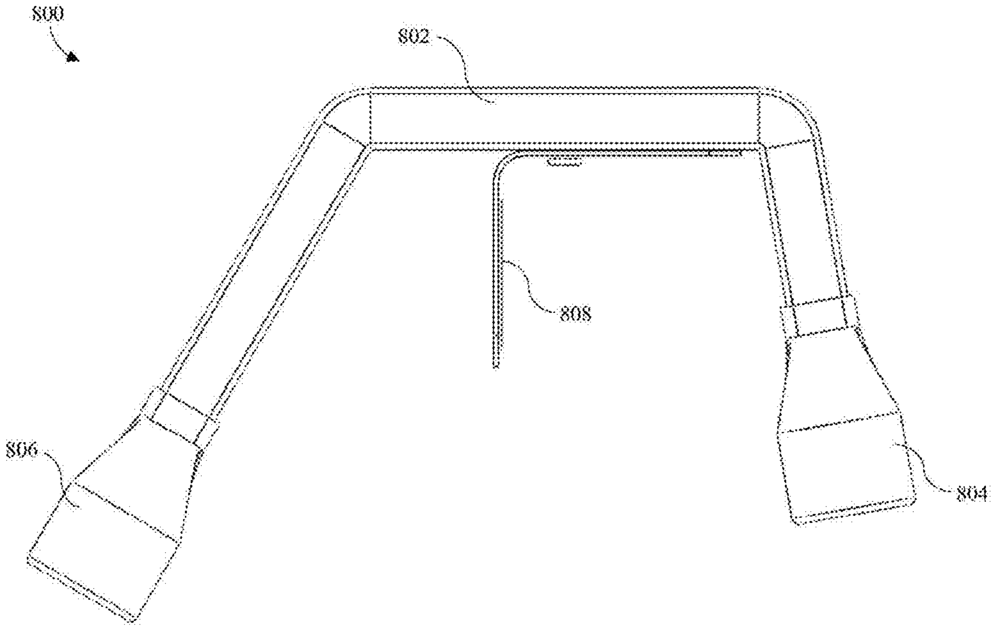
FIG. 11B is a plan view of a tube bridge connector for use in a personal heating and cooling system, in accordance with certain aspects of the present disclosure.

Referring now to FIG. 10, a functional perspective view of a trunk bridge 800 operably interfaced with thermal insulated cooler 128 for use in a personal heating and cooling system (e.g., system 100*a,b* as shown in FIGS. 1A-1H) is shown. FIGS. 11A-11B illustrate a perspective view and a plan view of trunk bridge 800. In accordance with certain aspects of the present disclosure, trunk bridge 800 comprises a bridge portion 802, a trunk connector portion 806, a tube connector portion 804 and a cooler clip 808. As shown in FIG. 10, cooler clip 808 is configured to retain bridge portion 802 to a side wall of thermal insulated cooler 128. Bridge portion 802 may comprise a hollow interior area configured to route a coolant supply line and a coolant return line therethrough. Trunk connector portion 806 is configured to enable a water-tight connection to trunk 108. Tube connector portion 804 is configured to enable a water-tight connection between a coolant supply line and a coolant return line (or otherwise route a coolant supply line and a coolant return line therethrough). In accordance with certain aspects of the present disclosure, a coolant supply line and a coolant return line are connected to tube connector portion 804 and are immersed in a volume of coolant (e.g., cold water) contained in an interior area thermal insulated cooler 128. In accordance with certain aspects of the present disclosure, trunk bridge 800 is configured to direct the volume of coolant from inside thermal insulated cooler 128, through bridge portion 802 via the coolant supply line and into trunk 108 for circulation in the personal heating and cooling system. After the volume of coolant has been circulated through the personal heating and cooling system, the volume of coolant flows back through trunk 108, into bridge portion 802 and back into thermal insulated cooler 128 via the coolant return line.

Figure 12:
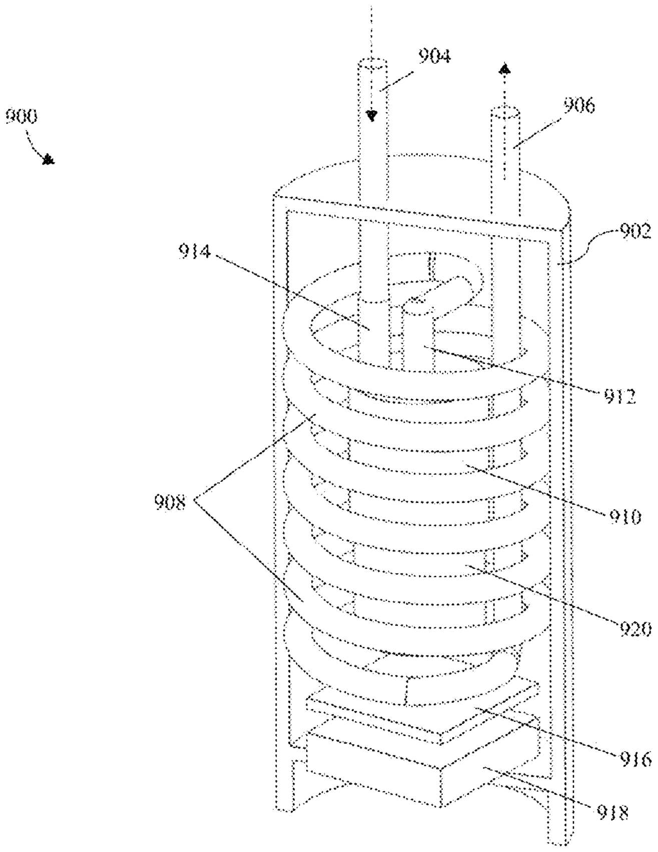
FIG. 12 is a component view of a closed loop pump for use in a personal heating and cooling apparatus and system, in accordance with certain aspects of the present disclosure.

Referring now to FIG. 12, a component view of a pump apparatus 900 for use in a personal heating and cooling apparatus and system of the present disclosure is shown. In accordance with certain aspects of the present disclosure, pump apparatus 900 may be configured as a closed loop pump of a personal heating and cooling apparatus and system (e.g., system 100*a,b* as shown in FIGS. 1A-1H). In accordance with certain embodiments, the personal heating and cooling apparatus and system may comprise a chair or pad comprising at least one coolant line installed therein. The at least one coolant line may be charged (i.e., filled) with a volume of liquid coolant (e.g., water). Pump apparatus 900 may be configured to circulate the volume of liquid coolant through coil a cooling coil 908 in order to chill the volume of coolant passing therethrough. In accordance with certain aspects of the present disclosure, pump apparatus 900 may comprise a return line 904 comprising a first end of the at least one coolant line. Return line 904 may direct returning coolant from the chair or pad to a pump inlet 914. A pump 910 may be operably engaged with a pump motor 920 to pump the coolant from pump inlet 914 to cooling coil inlet 912. In certain embodiments, pump 910 may comprise a positive displacement pump, such as a diaphragm pump, membrane pump, piston pump, plunger pump, and the like. Pump motor 920 may be operably engaged with a controller 916 comprising a printed circuit board electronics assembly and a battery 918 to control and power one or more operations of pump motor 920 in order to actuate pump 910.

In accordance with certain aspects of the present disclosure, pump 910 is configured to pump the coolant from pump inlet 914 to cooling coil inlet 912 and into cooling coil 908. Cooling coil 908 may comprise a copper coil or other thermally conductive metal coil. In accordance with certain aspects of the present disclosure, pump apparatus 900 comprises a water-tight housing 902. Water-tight housing 902 may be constructed of a thermally conductive metal. In accordance with certain aspects of the present disclosure, pump apparatus 900 is submerged in a volume of cold water (or other coolant) in order to chill cooling coil 908. The pressure created by pump 910 is operable to circulate a volume coolant through cooling coil 908. Cooling coil 908 functions as a heat exchanger in order to chill the volume of coolant passing through cooling coil 908. The chilled coolant is then routed to supply line 906 and back through the at least one coolant line installed in the chair or pad. A rate of circulation of the coolant may be controlled by increasing or decreasing a speed of pump motor 920.

Figure 13:
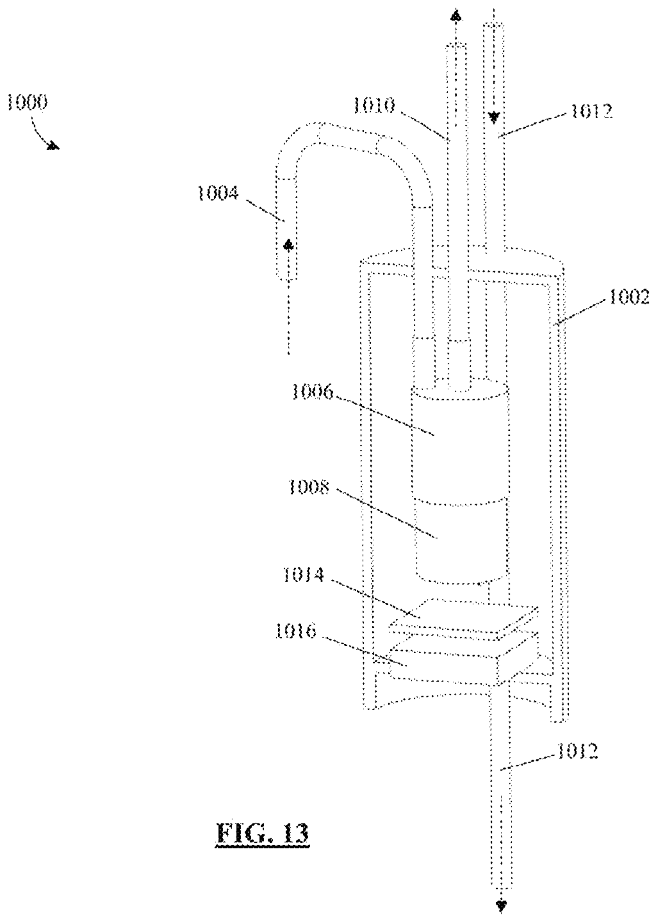
FIG. 13 is a component view of an open loop pump for use in a personal heating and cooling apparatus and system, in accordance with certain aspects of the present disclosure.

Referring now to FIG. 13, a component view of a pump apparatus 1000 for use in a personal heating and cooling apparatus and system is shown. In accordance with certain aspects of the present disclosure, pump apparatus 1000 may be configured as an open loop pump of a personal heating and cooling apparatus and system (e.g., system 100*a,b* as shown in FIGS. 1A-1H). In accordance with certain aspects of the present disclosure, pump apparatus 1000 may comprise a housing 1002 comprising an interior chamber in which a pump 1006, a pump motor 1008, a controller 1014 and a battery 1016 may be housed. In certain embodiments, pump 1006 may comprise a positive displacement pump, such as a diaphragm pump, membrane pump, piston pump, plunger pump, and the like. Pump motor 1008 may be operably engaged with controller 1014 and battery 1016. Controller 1014 may comprise a printed circuit board electronics assembly configured to command one or more operations of pump motor 1008. Battery 1016 may be configured to provide a flow of power to controller 1014 and pump motor 1008.

In accordance with certain aspects of the present disclosure, pump apparatus 1000 may comprise an intake line 1004 extending from an exterior to an interior portion of housing 1002. Intake line 1004 may be operably connected to pump 1006 at a first end. Intake line 1004 may comprise a flexible or semi-rigid tube configured to receive a flow of water therethrough. A second end of intake line 1004 may be submerged in a reservoir of cold water (or other coolant). In certain embodiments, the reservoir of cold water may comprise a thermal insulated cooler filled with ice water. Pump 1006 may be operably engaged with pump motor 1008 to create a negative pressure in intake line 1004 in order to draw a volume of water from the reservoir of cold water into intake line 1004 and into pump 1006. Pump 1006 is configured to pump the volume of cold water into an output line 1010. In accordance with various aspects of the present disclosure, output line 1010 comprises a first end of at least one cooling line that is routed through an interior portion of a chair or pad comprising a personal cooling apparatus (e.g., chair 102 as shown in FIGS. 1A-1H, and/or removable chair pad 200 as shown in FIGS. 2A-2B, and/or apparatus 300 as shown in FIGS. 3A-3C). In accordance with certain aspects of the present disclosure, the volume of cold water is circulated through a length of the at least one cooling line and is discharged back into the reservoir via a return line 1012. Pump apparatus 1000 may be configured to modify/control a rate of circulation of the volume of cold water by controlling a speed of pump motor 1008 according to one or more operational settings/controls of controller 1014.

Figure 14:
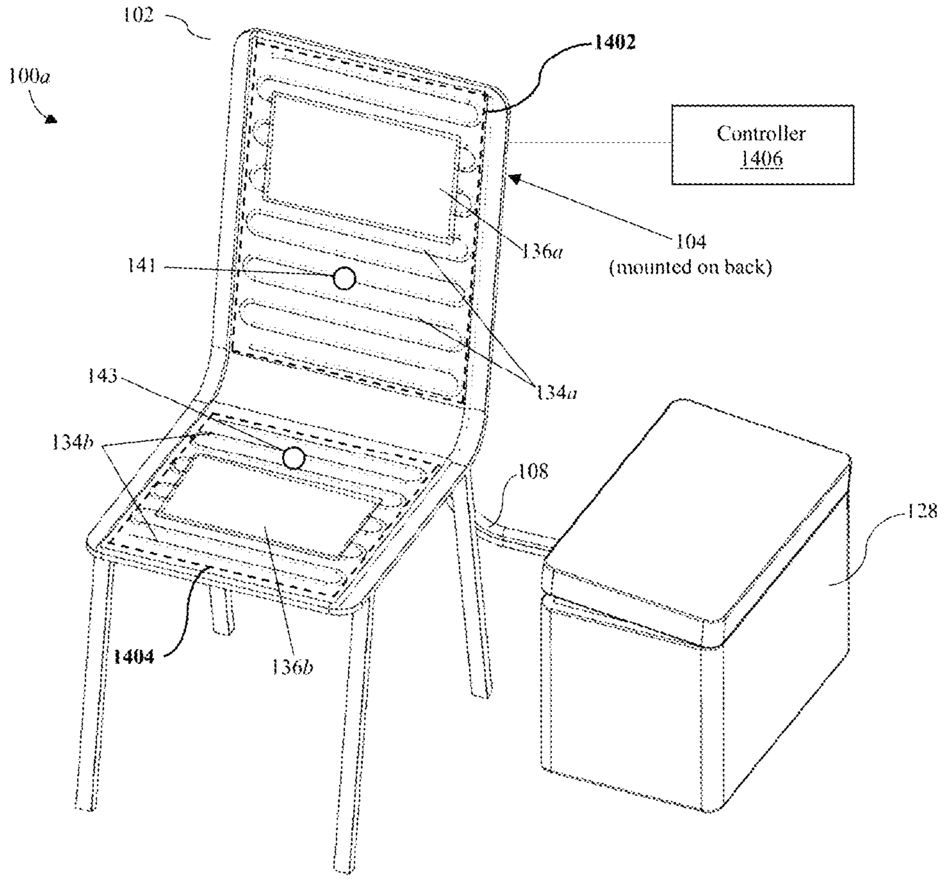
FIG. 14 is a perspective view of a personal heating and cooling system, in accordance with certain aspects of the present disclosure.

Referring now to FIG. 14, a perspective view of personal heating and cooling system **100*a* is shown. In accordance with certain aspects of the present disclosure, system 100*a* (and other embodiments of the present invention as described herein) may be configured to modulate a heating and cooling output of one or more heating and cooling zones 1402,1404. In accordance with certain aspects of the present disclosure, heating and cooling zone 1402 may comprise a back portion of chair 102 and heating and cooling zone 1404 may comprise a seat portion of chair 102. In accordance with certain embodiments, heating and cooling zone 1402 may be configured to provide a greater heating/cooling output than that of heating and cooling zone 1404. For example, the first length of flexible tubing 134*a* may comprise a greater surface area than the second length of flexible tubing 134*b*, thereby generating a greater cooling output at heating and cooling zone 1402. Likewise, first heating pad 136*a* may comprise a greater surface area and/or more heating elements than that of second heating pad 136*b*. In accordance with certain embodiments, system 100*a* may comprise a controller 1406 configured to control one or more functions of pump assembly 104, including increasing or decreasing the speed of the pump motor to increase and decrease the rate of circulation of the coolant and engaging and disengaging the pump motor to start and stop the circulation of the coolant through chair 102. In accordance with certain embodiments, controller 1406 may be configured to control one or more functions of first heating pad 136*a* and/or second heating pad 136*b*, including configuring a temperature setting, heating output duration, and engaging/disengaging a heating output. In accordance with certain aspects of the present disclosure system 100*a* may comprise one or more sensors 141,143. In accordance with certain embodiments, sensors 141,143 may comprise a temperature sensor and/or pressure sensor. Sensors 141,143 may be communicably engaged with controller 1406 to provide a sensor input thereto. In accordance with certain embodiments, controller 1406 may process an input from sensors 141,143 to determine the presence of a user in chair 102. Controller 1406 may further process an input from sensors 141,143 to determine a temperature of a surface of chair 102. In certain embodiments, controller 1406 may determine whether to engage or disengage a heating and/or cooling output in Zone 1402 and/or Zone 1404 based on the sensor input(s). In certain embodiments, controller 1406 may determine whether to modify or maintain a heating and/or cooling output in Zone 1402 and/or Zone 1404 based on the sensor input(s). In certain embodiments, controller 1406** may comprise one or more operations for optimizing a heating and/or cooling output based on one or more parameters. In accordance with certain aspects of the present disclosure, the one or more parameters may comprise parameter for user comfort, battery life/power consumption, safety, ice retention (in cooling applications) and the like.

Figure 15:
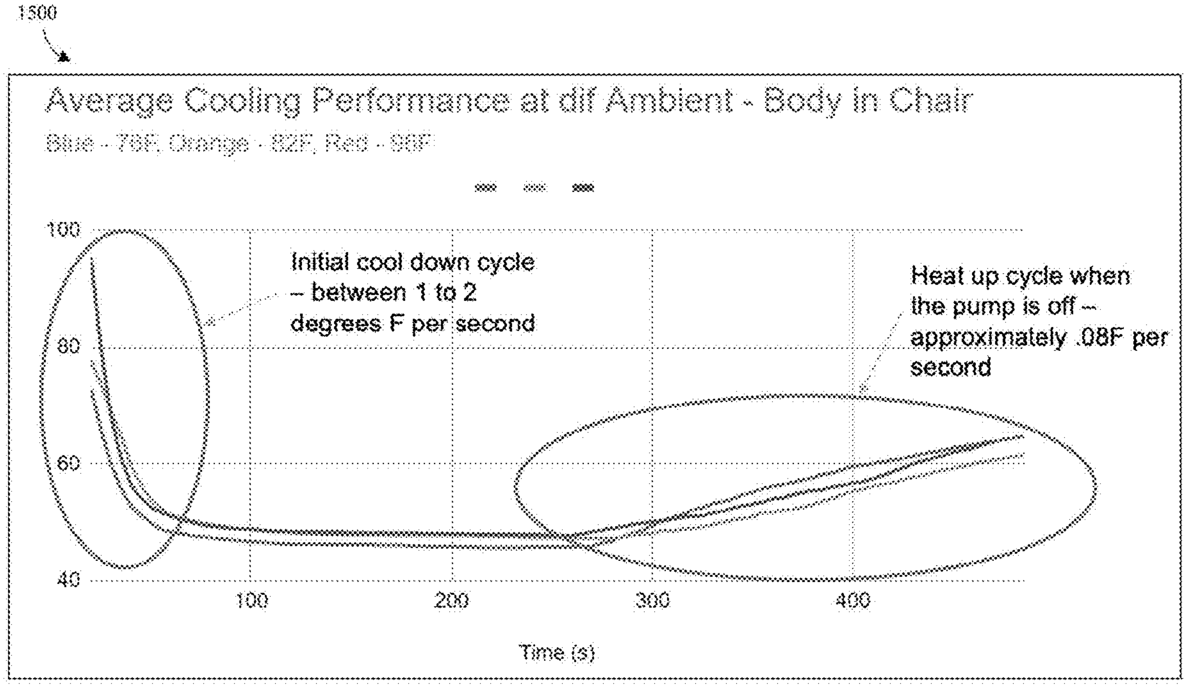
FIG. 15 is a plot of cooling performance as a function of time for a personal heating and cooling system, in accordance with certain aspects of the present disclosure.

Referring now to FIG. 15, a plot 1500 of cooling performance as a function of time for a personal heating and cooling system is shown. In accordance with certain aspects of the present disclosure, plot 1500 may comprise performance data for one or more of system **100*a*,*b*, as shown in FIGS. 1A-1H, and/or removable chair pad 200, as shown in FIGS. 2A-2B, and/or apparatus 300 as shown in FIGS. 3A-3C. As shown in plot 1500**, a pump motor speed of the personal heating and cooling system may be configured to circulate a volume of coolant through one or more coolant lines at a rate sufficient to lower a surface temperature of the chair by 1 to 2 degrees Fahrenheit per second until an optimal cooling temperature of approximately 50 degrees is obtained. In certain embodiments, a controller may be operably engaged with a temperature sensor to continuously measure the surface temperature of the chair/pad. The controller may be operable to control the pump motor to start/stop, speed up/slow down to maintain a desired temperature setpoint or threshold. In accordance with certain embodiments, the chair/pad may comprise an insulative batting material having an R-value sufficient to maintain a 0.08 degree/second increase in temperature when the pump motor is disengaged.

Figure 16:
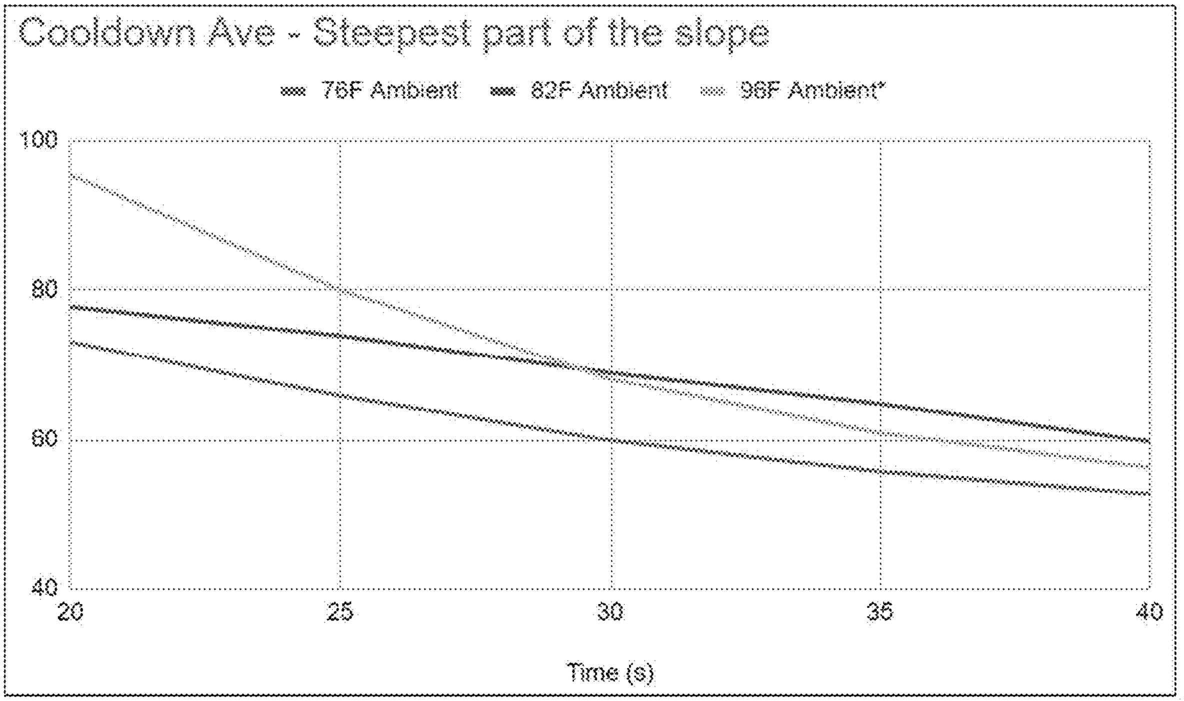
FIG. 16 is a plot of cooling performance as a function of time for a personal heating and cooling system, in accordance with certain aspects of the present disclosure.

Referring now to FIG. 16, a plot 1600 of cooling performance as a function of time for a personal heating and cooling system. In accordance with certain aspects of the present disclosure, plot 1600 may comprise performance data for one or more of system **100*a*,*b*, as shown in FIGS. 1A-1H, and/or removable chair pad 200, as shown in FIGS. 2A-2B, and/or apparatus 300, as shown in FIGS. 3A-3C. In accordance with certain embodiments, the personal heating and cooling system may be configured to circulate a volume of coolant through one or more coolant lines at a rate sufficient to obtain an average cooldown performance at the different ambient temperatures shown in plot 1600**.

Figure 17:
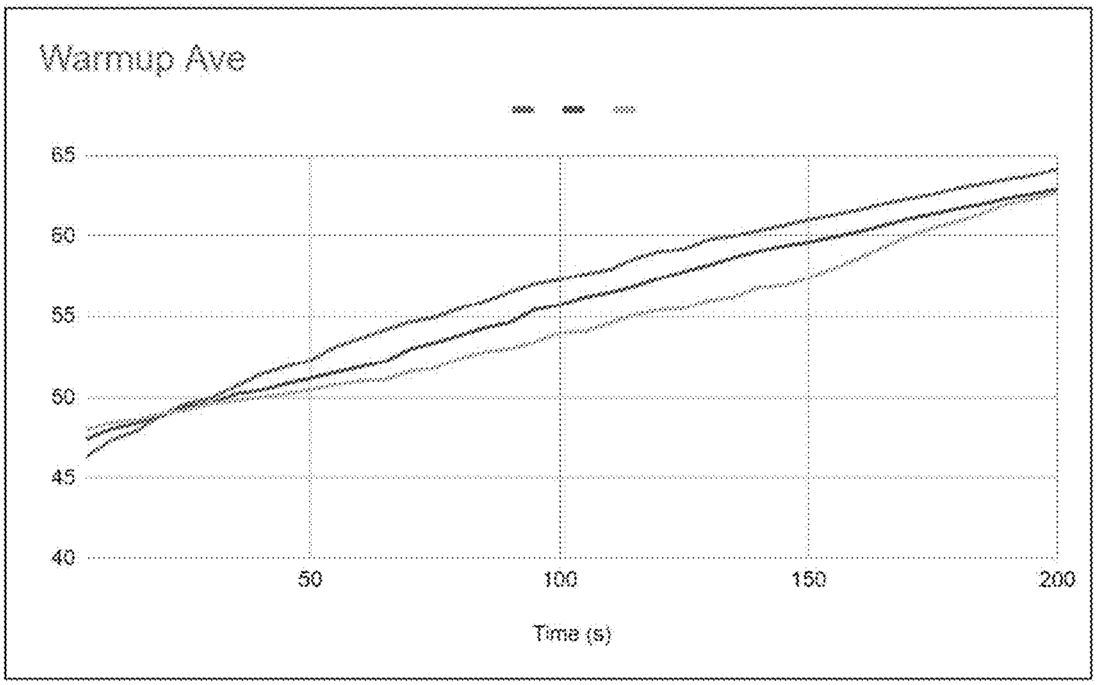
FIG. 17 is a plot of heating performance as a function of time for a personal heating and cooling system, in accordance with certain aspects of the present disclosure.

Referring now to FIG. 17, a plot of heating performance as a function of time for a personal heating and cooling system is shown. In accordance with certain aspects of the present disclosure, plot 1700 may comprise performance data for one or more of system 100*a,b*, as shown in FIGS. 1A-1H, and/or removable chair pad 200, as shown in FIGS. 2A-2B, and/or apparatus 300 as shown in FIGS. 3A-3C. In accordance with certain embodiments, the personal heating and cooling system may be configured to produce a heating output at one or more heating pads sufficient to obtain an average warming performance at the different ambient temperatures shown in plot 1600.

Figure 18:
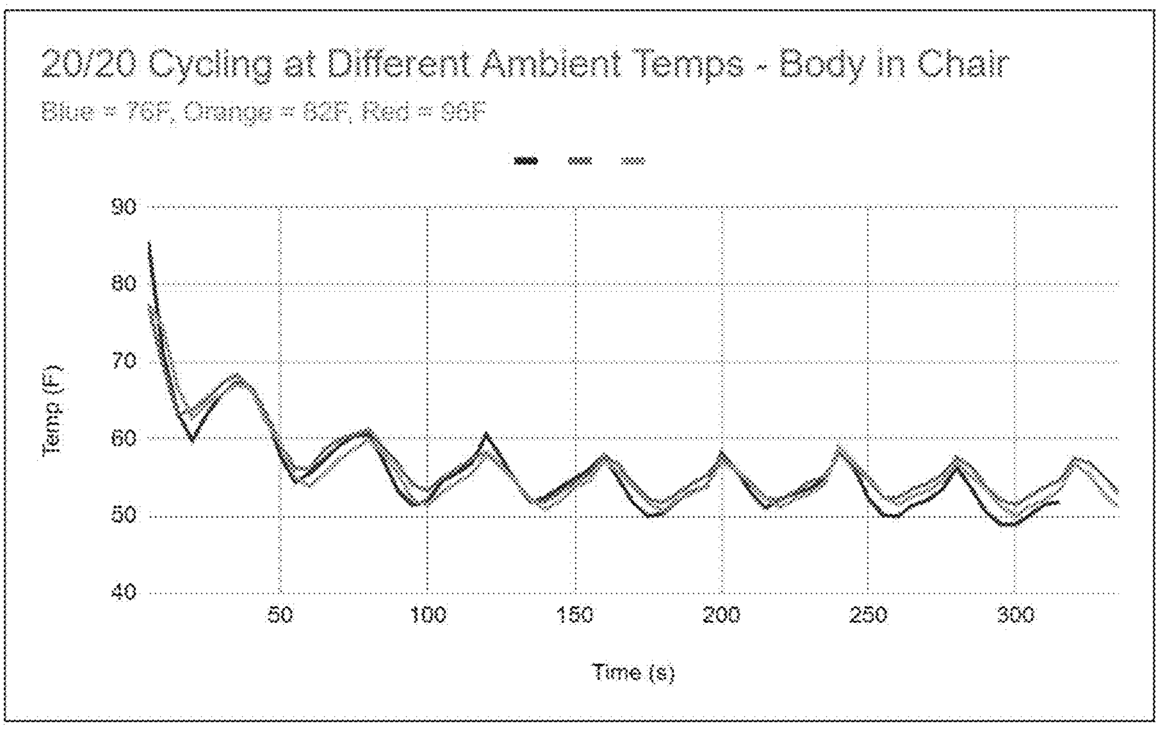
FIG. 18 is a plot of cooling cycling as a function of time for a personal heating and cooling system, in accordance with certain aspects of the present disclosure.

Referring now to FIG. 18, a plot 1800 of cooling cycling as a function of time for a personal heating and cooling system is shown. In accordance with certain aspects of the present disclosure, plot 1800 may comprise performance data for one or more of system 100*a,b*, as shown in FIGS. 1A-1H, and/or removable chair pad 200, as shown in FIGS. 2A-2B, and/or apparatus 300 as shown in FIGS. 3A-3C. In accordance with certain embodiments, a controller of the personal heating and cooling system may be configured to optimize a cooling output for improved comfort and energy consumption by cycling a pump motor ON/OFF at 20 second intervals. In accordance with certain aspects of the present disclosure, a pump motor speed of the personal heating and cooling system may be configured to circulate a volume of coolant through one or more coolant lines at a rate sufficient to lower/maintain a surface temperature of the chair/pad at different ambient temperatures when cycled ON/OFF at 20 second intervals in accordance with the performance data included in plot 1800.

Figure 19:
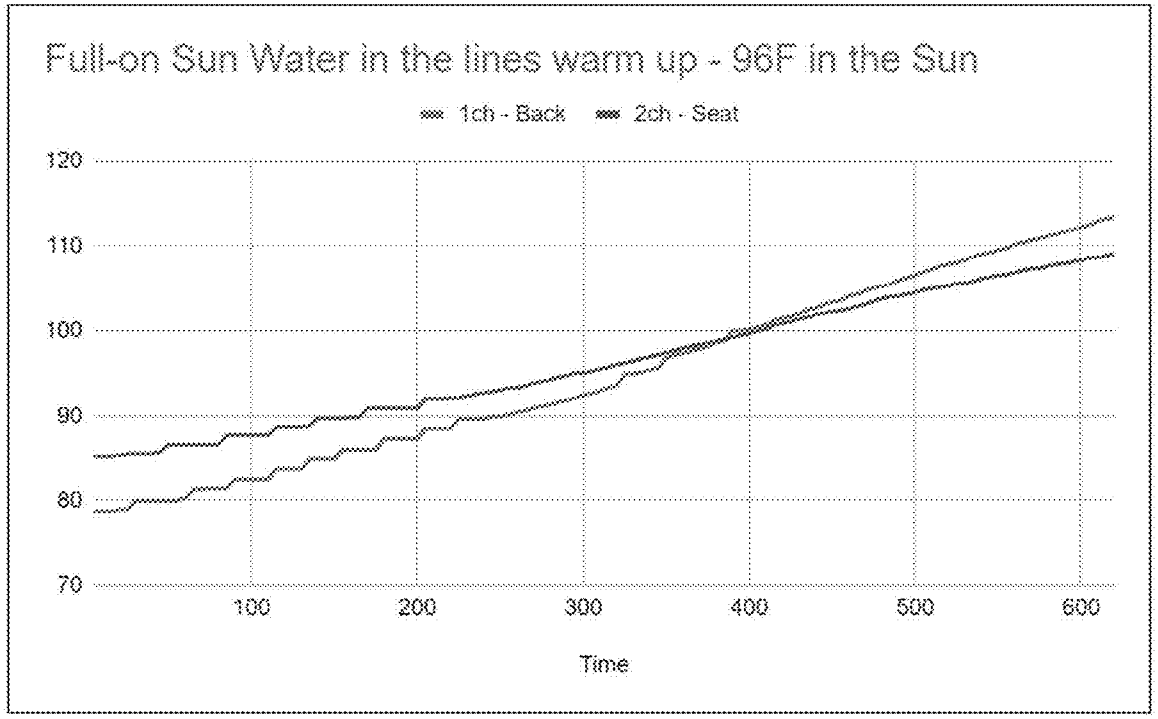
FIG. 19 is a plot of warming of coolant lines over time in full sun for a personal heating and cooling system, in accordance with certain aspects of the present disclosure.

Referring now to FIG. 19, a plot 1900 of warming of coolant lines over time in full sun for a personal heating and cooling system is shown. In accordance with certain aspects of the present disclosure, plot 1900 may comprise performance data for one or more of system 100*a,b*, as shown in FIGS. 1A-1H, and/or removable chair pad 200, as shown in FIGS. 2A-2B, and/or apparatus 300 as shown in FIGS. 3A-3C. In accordance with certain embodiments, the chair/pad may comprise an insulative batting material and/or an insulative exterior shell material having an R-value sufficient to maintain a per second increase in temperature when the pump motor is disengaged under the conditions as shown in plot 1900.

Figure 20:
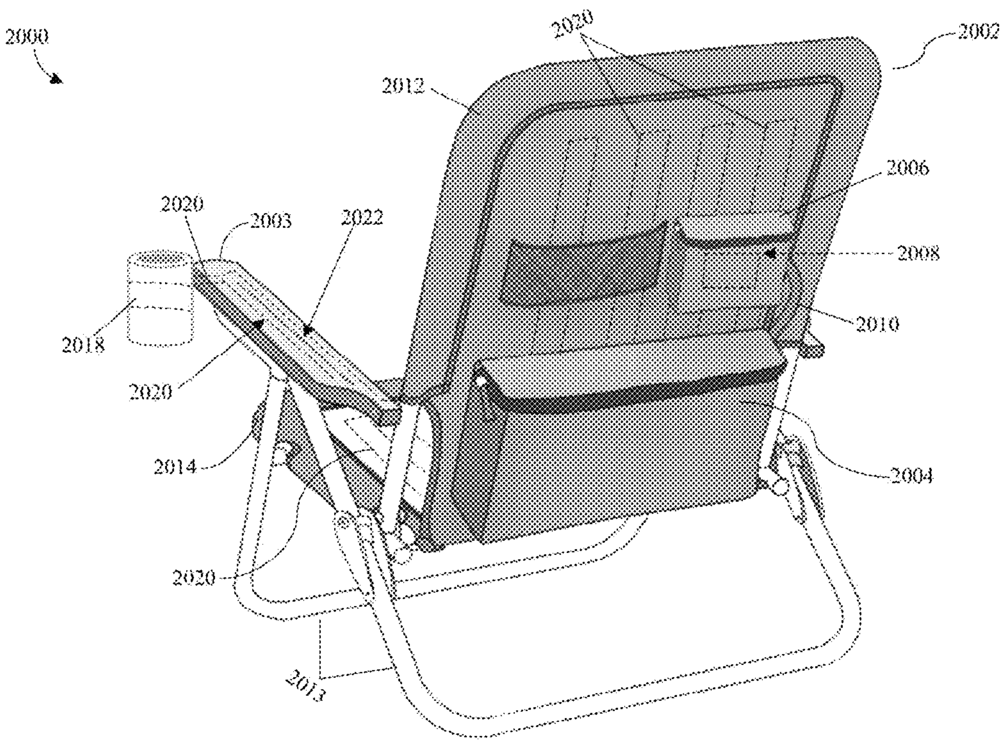
FIG. 20 is a perspective view of a personal heating and cooling apparatus and system, in accordance with certain aspects of the present disclosure.

Referring now to FIG. 20, a perspective view of a personal heating and cooling system 2000 is shown. In accordance with certain aspects of the present disclosure, system 2000 may comprise a chair 2002 comprising a back portion 2012, a seat portion 2014, legs 2013 and arm rests 2003. Chair 2002 may have a cooler portion 2004 disposed on a surface of back portion 2012. Cooler portion 2004 may be constructed from a thermal insulated and waterproof material and may be configured to retain a volume of ice/water therein. Chair 2002 may further comprise a pump pocket 2006 disposed on the surface of back portion 2012. In accordance with certain aspects of the present disclosure, system 2000 may comprise a pump assembly 2008 being selectively stored in pump pocket 2006. In certain embodiments, pump assembly 2008 may be embodied as pump assembly 400, as shown in FIGS. 4A-4B, and/or pump assembly 500, as shown in FIG. 5. In certain embodiments, pump assembly 2008 may be embodied as pump apparatus 900, as shown in FIG. 12, and/or pump apparatus 1000, as shown in FIG. 13. In certain embodiments, pump assembly 2008 may comprise at least one controller and at least one battery configured to control/power at least one pump motor and at least one heating element 2022.

In accordance with certain aspects of the present disclosure, system 2000 may comprise a trunk 2010 comprising a coolant supply line and a coolant return line. Trunk 2010 may be operably configured to deliver a volume of water (i.e., coolant) from cooler portion 2004 to pump assembly 2008 via the coolant supply line. In accordance with certain aspects of the present disclosure, pump assembly 2008 is configured to circulate the volume of water through coolant lines 2020. Coolant lines 2020 may be routed through one or more internal areas of chair 2002, including an internal area of back portion 2012, seat portion 2014 and arm rest 2003. In certain embodiments, chair 2002 may comprise an insulated cup holder 2018 coupled to arm rest 2003. In certain embodiments, coolant lines 2020 may be routed through an internal area of the insulated cup holder 2018. In accordance with certain aspects of the present disclosure, once the volume of coolant is circulated through the entire length of cooling lines 2022, the coolant is circulated back to cooler portion 2004 via the return line of trunk 2010. In accordance with certain aspects of the present disclosure, system 2002 may comprise one or more electric heating elements 2022 housed in one or more internal areas of chair 2002, including an internal area of back portion 2012, seat portion 2014 and arm rest 2003. A heating output of heating elements 2022 may be controlled by a controller of pump assembly 2008 and may be configurable in response to one or more user inputs via one or more user controls (i.e., interface).

Figure 21:
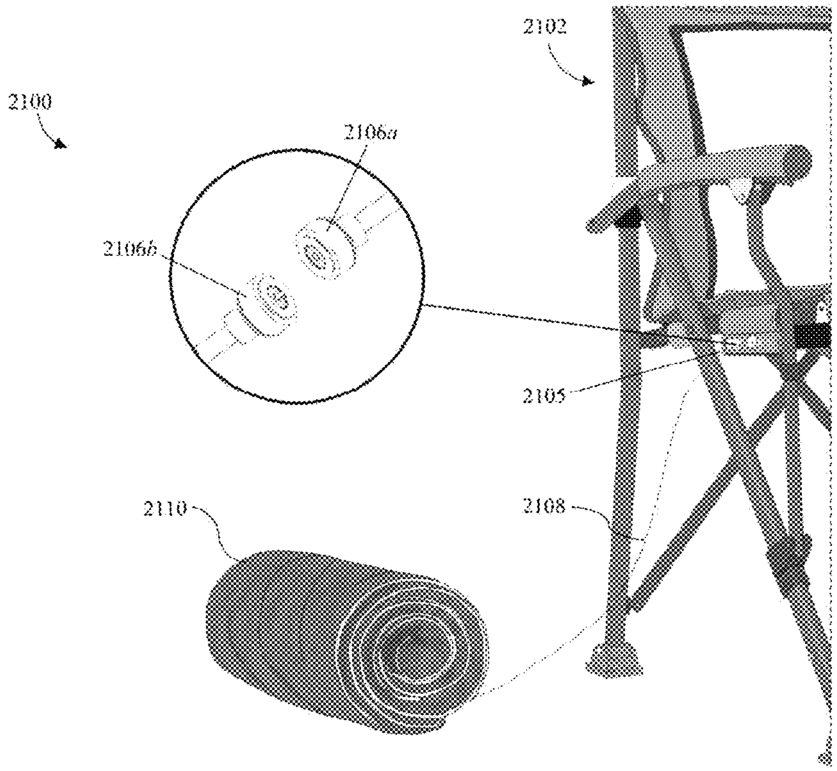
FIG. 21 is a functional perspective view of a personal heating and cooling system, in accordance with certain aspects of the present disclosure.

Referring now to FIG. 21, a functional perspective view of a personal heating and cooling system 2100 is shown. In accordance with certain aspects of the present disclosure, personal heating and cooling system 2100 may be embodied as system 100*a,b*, as shown in FIGS. 1A-1H, and/or removable chair pad 200, as shown in FIGS. 2A-2B, and/or apparatus 300 as shown in FIGS. 3A-3C. In accordance with certain aspects of the present disclosure, system 2100 may comprise a chair 2102 comprising one or more coolant lines and/or heating elements contained therein. In accordance with certain embodiments, system 2100 may comprise one or more accessory apparatus that are configured to be selectively engaged with chair 2102. In accordance with certain embodiments, an accessory apparatus may comprise a heated blanket 2110. In certain embodiments, heated blanket 2110 may comprise a power cable 2108. Power cable 2108 may comprise a male end of a magnetic power connector 2106*b* (or other power interface, such as a USB connector) configured to interface with a female end of a magnetic power connector 2106*a* (or other power interface, such as a USB port) of an electronics assembly 2105 of chair 2102. Electronics assembly 2105 may be configured to provide a power output from at least one battery to heated blanket 2110 via power cable 2108.

Figure 22:
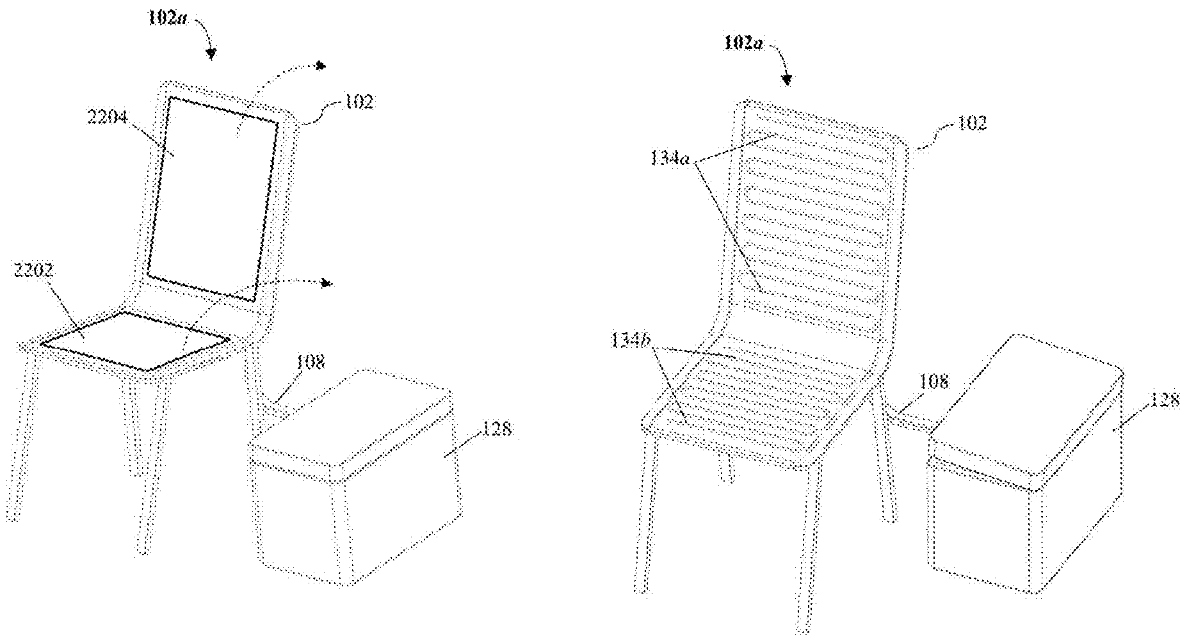
FIG. 22 is a functional perspective view of a personal heating and cooling system, in accordance with certain aspects of the present disclosure.

Referring now to FIG. 22, a functional perspective view of personal heating and cooling system 102*a* is shown. In accordance with certain aspects of the present disclosure, the personal heating and cooling system may comprise any of the alternative embodiments discussed herein. In accordance with certain aspects of the present disclosure, system 102*a* may comprise one or more of a removeable back pad 2204 and a removeable seat pad 2202. In certain embodiments, a user may selectively remove one or both of removeable back pad 2204 and removeable seat pad 2202 to expose the first length of flexible tubing 134*a* and/or the second length of flexible tubing 134*b*.

Figure 23:
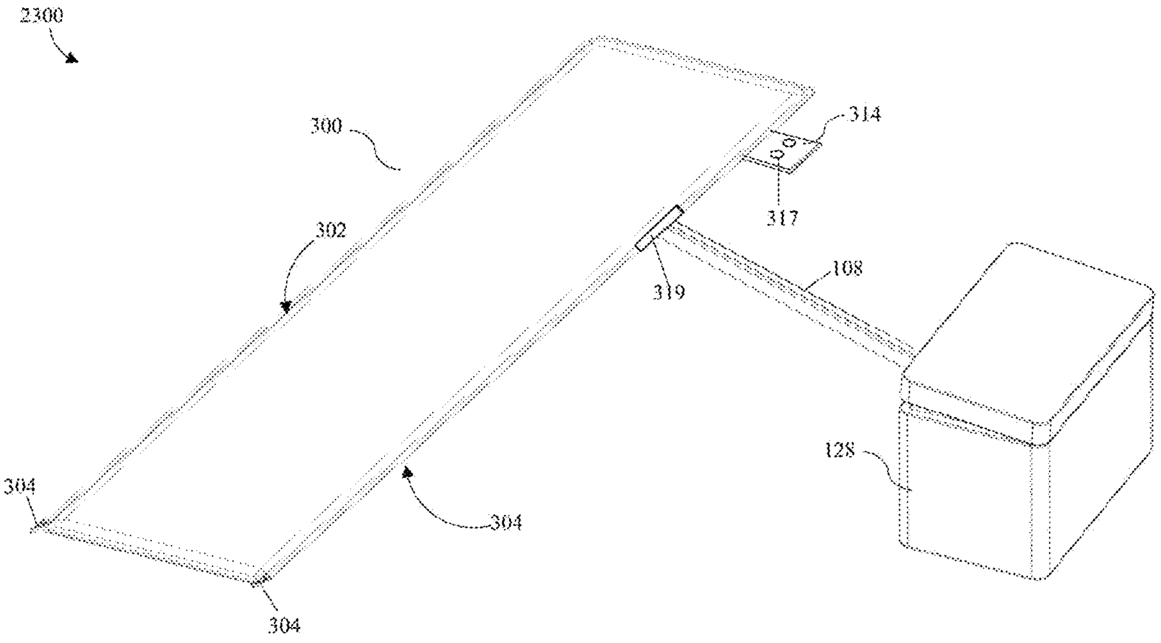
FIG. 23 is a perspective view of a personal heating and cooling system, in accordance with certain aspects of the present disclosure.

Referring now to FIG. 23, a perspective view of personal heating and cooling system 2300 comprising personal heating and cooling apparatus 300 operably interfaced with trunk line 108 and thermal insulated cooler 128 is shown. In accordance with certain aspects of the present disclosure, system 2300 may comprise an electronics assembly 314 comprising at least one battery and a controller. System 2300 may further comprise a pump assembly 319 comprising at least one pump and pump motor configured to circulate a volume of water from thermal insulated cooler 128 via trunk 108 and through the coolant lines of apparatus 300. Electronics assembly 314 may further comprise one or more user controls configured to command one or more heating and/or cooling operations of system 2300. In accordance with certain aspects of the present disclosure, system 2300 comprises a form factor configured enable apparatus 300 to be laid flat on the ground (or other flat surface such as an air mattress or a baby crib or stroller). In accordance with certain aspects of the present disclosure, a form factor of system 2300 enables one or more use cases, including but not limited to, a heated and cooled sleeping pad, a heated and cooled pet bed, a heated and cooled field/beach blanket and the like.

Figure 24:
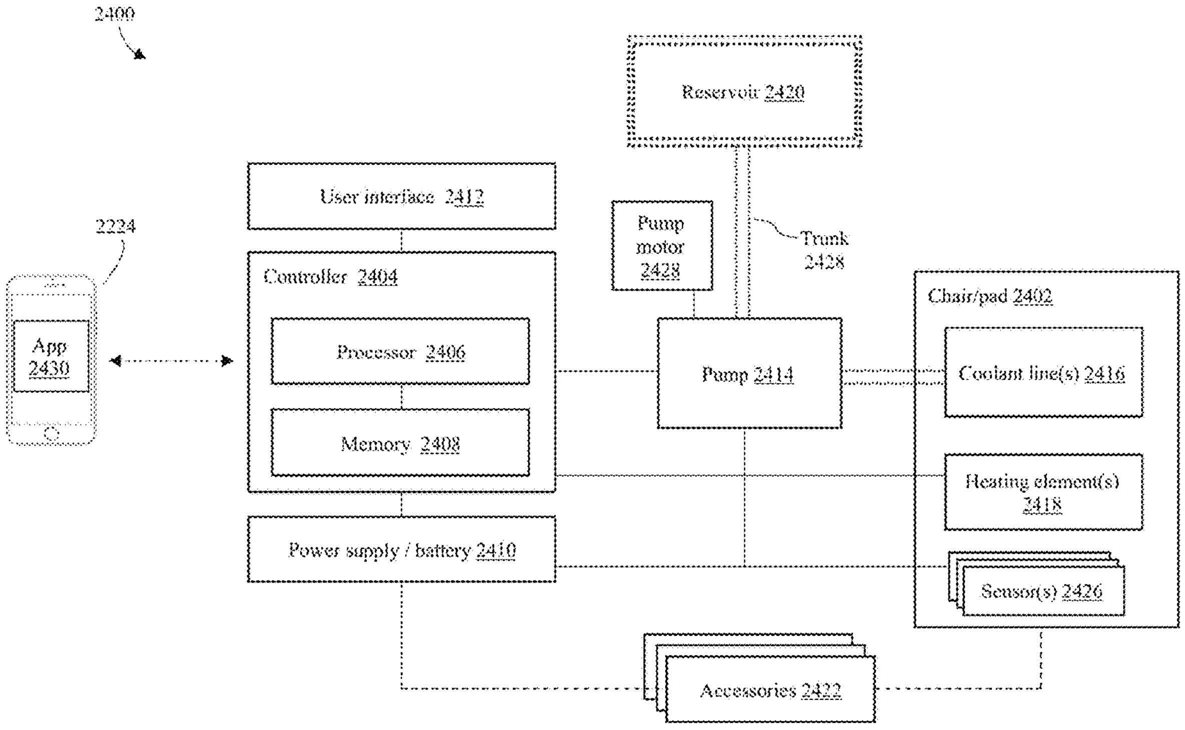
FIG. 24 is a functional block diagram of a personal heating and cooling system, in accordance with certain aspects of the present disclosure.

Referring now to FIG. 24, a functional block diagram of a personal heating and cooling system 2400 is shown. In accordance with certain aspects of the present disclosure, system 2400 may be embodied as one or more of system 100*a,b*, as shown in FIGS. 1A-1H, and/or removable chair pad 200, as shown in FIGS. 2A-2B, and/or apparatus 300 as shown in FIGS. 3A-3C and/or any of the other embodiments described herein. In accordance with certain aspects of the present disclosure, system 2400 may comprise a chair or pad 2402 comprising one or more coolant lines 2416 being routed in an internal area of chair or pad 2402, including a back portion and a seat portion of chair or pad 2402. In certain embodiments, coolant lines 2416 may be constructed from flexible or semi-rigid tubes and may comprise tubing having a 1/16" internal diameter and 1/8" outer diameter. Coolant lines 2416 may be constructed from a mildew resistant material and may comprise a thermally insulated tubing. Chair or pad 2402 may further comprise one or more heating elements 2418 disposed in one or more internal areas of chair or pad 2402, including a back portion and a seat portion of chair or pad 2402. In certain embodiments, heating elements 2418 may comprise one or more conductive wires and/or may comprise one or more electric heating pads. In certain embodiments, chair or pad 2402 may further comprise one or more sensors 2426 being located in one or more internal areas of chair or pad 2402 and/or disposed on one or more surface of chair or pad 2402 (e.g., at the back portion and/or the seat portion of chair or pad 2402). In accordance with certain embodiments, sensors 2426 may include one or more temperature sensor, humidity sensor, pressure sensor, accelerometer and/or other environmental or occupant sensors.

In accordance with further aspects of the present disclosure, system 2400 may comprise at least one pump 2414 operably engaged with a pump motor 2428. Pump 2414 may be configured as any of the pump embodiments described herein. Pump 2414 may comprise a positive displacement pump, such as a diaphragm pump, membrane pump, piston pump, plunger pump, and the like. Pump 2414 may be operably engaged with pump motor 2428 to pump a volume of water from a reservoir 2420 into coolant lines 2416 via a trunk 2428. Trunk 2428 may comprise a supply line and a return line.

In accordance with certain aspects of the present disclosure, system 2400 may further comprise a controller 2404. Controller 2404 may comprise a processor 2406 and a non-transitory computer readable memory device 2408 have instructions stored thereon for commanding one or more operations of processor 2404. Controller 2404 may be operably engaged with pump 2414 and heating element(s) 2418 via one or more bus or wireline interface to control one or more operations of pump 2414 and heating element(s) 2418. Controller 2404 may be communicably engaged with sensor(s) 2426 to receive and process one or more sensor inputs. In accordance with certain aspects of the present disclosure, controller 2404 may configure one or more operational mode(s) and/or setting(s) in response to the one or more sensor inputs; including, modulating an operation of pump 2414 and/or heating element(s) 2418 to modify a cooling or heating output of chair or pad 2402. System 2400 may further comprise a power supply or battery 2410 operably engaged with controller 2404, pump motor 2428, heating elements 2418 and sensors 2426. In certain embodiments, system 2400 may comprise a user interface 2412 communicably engaged with controller 2404. User interface 2412 may comprise one or more buttons or other input modalities configured to provide a command signal to controller 2404 in response to a user input. In accordance with certain aspects, controller 2404 may be configured to command an operation of pump 2414 and/or heating element(s) 2418 to modify/configure a cooling or heating output of chair or pad 2402 in response to the user input at the user interface.

In accordance with certain aspects of the present disclosure, system 2400 may comprise one or more accessories 2422 configured to selectively interface with chair or pad 2402 and/or power supply/battery 2410. In accordance with certain aspects of the present disclosure, accessories 2422 may comprise one or more heated blanket, fan, light, heat/cooled cup holder, radio/speaker, sweatshirt/clothing, heater, arc lighter and other electronic appliances. In accordance with certain aspects of the present disclosure, system 2400 may comprise a smart phone 2224 communicably engaged with controller 2404 via a wireless data transfer interface (e.g., BLUETOOTH). Smart phone 2224 may comprise a mobile application 2430 configured to command one or more operations of controller 2404 and visualize one or more data output from controller 2404 (e.g., temperature setting, battery life, coolant temperature, operational mode, usage statistics and the like).

The terminology used herein is for describing particular embodiments only and is not intended to be limiting of the embodiments. As used herein, the singular forms “a,” “an,” and “the” are intended to include the plural forms as well, unless the context clearly indicates otherwise. It will be further understood that the terms “comprises,” “comprising,” “includes,” and/or “including,”, and variants thereof, when used herein, specify the presence of stated features, steps, operations, elements, and/or components, but do not preclude the presence or addition of one or more other features, steps, operations, elements, components, and/or groups thereof. As used herein, “exemplary” means serving as an example or illustration and does not necessarily denote ideal or best.

It will be understood that when an element is referred to as being “coupled,” “connected,” “disposed on,” or “responsive” to another element, it can be directly coupled, connected, or responsive to the other element, or intervening elements may also be present. In contrast, when an element is referred to as being “directly coupled,” “directly connected,” or “directly responsive” to another element, there are no intervening elements present. As used herein, the term “and/or” includes any and all combinations of one or more of the associated listed items.

Spatially relative terms, such as “above,” “below,” “upper,” “lower,” “top, “bottom,” and the like, may be used herein for ease of description to describe one element or feature’s relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly. Well-known functions or constructions may not be described in detail for brevity and/or clarity.

It will be understood that, although the terms "first," "second," etc. may be used herein to describe various elements, these elements should not be limited by these terms. These terms are only used to distinguish one element from another. Thus, a first element could be termed a second element without departing from the teachings of the present embodiments. Unless otherwise defined, all terms (including technical and scientific terms) used herein have the same meaning as commonly understood by one of ordinary skill in the art to which these embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The present disclosure includes that contained in the appended claims as well as that of the foregoing description. Although this invention has been described in its exemplary forms with a certain degree of particularity, it is understood that the present disclosure of has been made only by way of example and numerous changes in the details of construction and combination and arrangement of parts may be employed without departing from the spirit and scope of the invention. Therefore, it will be apparent to those skilled in the art that various modifications and variations can be made to the disclosed embodiments without departing from the scope or spirit of the invention. In view of the foregoing, it is intended that the invention covers modifications and variations of this disclosure within the scope of the following claims and their equivalents.

What is claimed is:

1. A personal comfort system, comprising:

an elongated pad comprising an upper fabric surface and a lower fabric surface, wherein the elongated pad is configured to be selectively disposed on a back portion and a seat portion of a chair, wherein the elongated pad comprises a length of flexible tubing disposed on an internal area of the elongated pad and housed between the upper fabric surface and the lower fabric surface, wherein the length of flexible tubing extends between a first end comprising a coolant inlet and a second end comprising a coolant outlet, wherein the flexible tubing comprises plastic tubing arranged on the internal area in a plurality of evenly spaced, parallel rows, a trunk comprising a coolant supply line and a coolant return line;

an adapter portion coupled to a first end of the trunk, wherein the adapter portion comprises a drain-plug adapter configured to selectively interface with a drain portion of an insulated cooler, wherein the drain-plug adapter comprises a stem portion configured to extend through the drain portion of the insulated cooler, a supply line aperture, a return line aperture, a supply channel extending through the drain-plug adapter to the supply line aperture, and a return channel extending through the drain-plug adapter to the return line aperture, a filter basket configured to be secured to the stem portion of the drain-plug adapter within an internal area of the insulated cooler;

a pump comprising a first coupling configured to be selectively coupled with the first end and the second end of the length of flexible tubing and a second coupling configured to be removably coupled with the coolant supply line and the coolant return line of the trunk, wherein the pump is operably configured to circulate a volume of coolant from the coolant supply line of the trunk through the length of flexible tubing and to the coolant return line of the trunk; and a power supply operably engaged with the pump to provide a flow of power to the pump.

2. The personal comfort system of claim 1 wherein the filter basket is configured to retain the drain-plug adapter in place relative to the drain portion of the insulated cooler.

3. The personal comfort system of claim 1 wherein the second coupling comprises a supply channel configured to establish a watertight connection with the coolant supply line of the trunk and a return channel configured to establish a watertight connection with the coolant return line of the trunk.

4. The personal comfort system of claim 1 wherein the elongated pad comprises a back portion and a seat portion and the length of flexible tubing in the back portion and the seat portion is oriented substantially vertically such that, when the elongated pad is disposed on a chair having a foldable frame, the flexible tubing does not kink when the chair is folded.

5. The personal comfort system of claim 3 further comprising at least one heating pad disposed on the internal area of the elongated pad between the upper fabric surface and the lower fabric surface, wherein the at least one heating pad is operably engaged with at least one controller and the power supply to regulate a heating output according to one or more operational settings of the at least one controller and wherein the at least one heating pad comprises a first heating zone and a second heating zone, the at least one controller configured to selectively regulate power between the first heating zone and the second heating zone.

6. The personal comfort system of claim 3 further comprising at least one thermal sensor communicably engaged with at least one controller, wherein the at least one controller is configured to regulate the flow of power to the pump in response to an input from the at least one thermal sensor to cycle the pump on and off according to one or more temperature thresholds.

7. The personal comfort system of claim 3 further comprising at least one pressure sensor communicably engaged with at least one controller, the at least one pressure sensor disposed within the elongated pad between the upper fabric surface and the lower fabric surface, wherein the at least one controller is configured to regulate the flow of power to the pump in response to an input from the at least one pressure sensor indicative of seat occupancy exceeding a threshold.

8. The personal comfort system of claim 1, wherein the elongated pad comprises a connector portion configured to selectively couple the elongated pad to the chair.

9. The personal comfort system of claim 8, wherein the connector portion comprises a hood portion configured to selectively interface with the back portion of the chair.

10. The personal comfort system of claim 1, wherein the elongated pad comprises a non-slip fabric disposed on a bottom surface of the elongated pad.

11. The personal comfort system of claim 1, wherein the pump comprises a first tube connector configured to establish a removable watertight connection with the first end of the length of flexible tubing and a second tube connector configured to establish a removable watertight connection with the second end of the length of flexible tubing.

12. The personal comfort system of claim 11, wherein the pump is configured to be selectively disconnected from both the trunk and the length of flexible tubing.

13. The personal comfort system of claim 1, wherein the supply channel extends from a distal end of the stem portion to the supply line aperture.

14. The personal comfort system of claim 1, wherein the return channel extends from a return port disposed on a lateral portion of the stem portion to the return line aperture.

15. The personal comfort system of claim 1, wherein the drain-plug adapter is configured to establish a watertight connection between the supply line aperture and the coolant supply line of the trunk and between the return line aperture and the coolant return line of the trunk.

16. A personal comfort system, comprising:

an insulated cooler comprising an internal area configured to receive a volume of coolant and a drain portion in fluid communication with the internal area;

a drain-plug adapter selectively interfaced with the drain portion of the insulated cooler, the drain-plug adapter comprising a stem portion extending through the drain portion, a supply channel, and a return channel;

a trunk coupled to the drain-plug adapter, the trunk comprising a coolant supply line in fluid communication with the supply channel and a coolant return line in fluid communication with the return channel;

a filter basket secured to the stem portion of the drain-plug adapter and positioned within the internal area of the insulated cooler;

a pump removably coupled to the trunk, the pump comprising a first pump connection in fluid communication with the coolant supply line and a second pump connection in fluid communication with the coolant return line;

an elongated pad configured to be selectively disposed on a chair, the elongated pad comprising a length of flexible tubing housed between an upper fabric surface and a lower fabric surface of the elongated pad, the length of flexible tubing comprising a coolant inlet removably coupled to the pump and a coolant outlet removably coupled to the pump, wherein the pump is configured to circulate coolant from the internal area of the insulated cooler, through the supply channel of the drain-plug adapter, through the coolant supply line of the trunk, through the length of flexible tubing of the elongated pad, through the coolant return line of the trunk, through the return channel of the drain-plug adapter, and back into the internal area of the insulated cooler; and a power supply operably engaged with the pump to provide power to the pump.

* * * * *